(12) United States Patent
Grandfils et al.

(10) Patent No.: US 9,616,089 B2
(45) Date of Patent: Apr. 11, 2017

(54) POLYMERIC SYNTHETIC ANTIDOTE

(71) Applicant: Universite de Liege, Angleur (BE)

(72) Inventors: Christian Grandfils, Liege (BE);
Lucas Flebus, Soheit-Tinlot (BE);
Chantal Sevrin, Liege (BE)

(73) Assignee: UNIVERSITE DE LIEGE, Angleur (BE)

( * ) Notice: Subject to any disclaimer, the term of this patent is extended or adjusted under 35 U.S.C. 154(b) by 0 days.

(21) Appl. No.: 14/911,435

(22) PCT Filed: Aug. 8, 2014

(86) PCT No.: PCT/EP2014/067081
§ 371 (c)(1),
(2) Date: Feb. 10, 2016

(87) PCT Pub. No.: WO2015/028286
PCT Pub. Date: Mar. 5, 2015

(65) Prior Publication Data
US 2016/0193246 A1 Jul. 7, 2016

(30) Foreign Application Priority Data
Aug. 29, 2013 (EP) .................................. 13182277

(51) Int. Cl.
A61K 31/785 (2006.01)
A61K 9/00 (2006.01)
A61K 47/34 (2017.01)
A61K 31/78 (2006.01)
A61K 31/727 (2006.01)
C08F 120/34 (2006.01)
B01J 41/14 (2006.01)

(52) U.S. Cl.
CPC .......... A61K 31/785 (2013.01); A61K 9/0019 (2013.01); A61K 31/727 (2013.01); A61K 31/78 (2013.01); A61K 47/34 (2013.01); B01J 41/14 (2013.01); C08F 120/34 (2013.01)

(58) Field of Classification Search
None
See application file for complete search history.

(56) References Cited

U.S. PATENT DOCUMENTS

2012/0308546 A1   12/2012   Kizhakkedathu et al.

FOREIGN PATENT DOCUMENTS

JP   2012 029831   2/2012

OTHER PUBLICATIONS

Nakayama, Y., et al., "Thermoresponsive Heparin Bioconjugate as Novel Aqueous Antithrombogenic Coating Material", Bioconjugate Chemistry, vol. 22, (2011), pp. 193-199, XP055089661.
International Search Report Issued on Oct. 21, 2014 in International Application No. PCT/EP2014/067081 filed Aug. 8, 2014.

Primary Examiner — Aradhana Sasan
(74) Attorney, Agent, or Firm — Jacobson Holman, PLLC.

(57) ABSTRACT

A polymer of formula (I) where $X_1$ and $X_2$ respectively represent the alpha and omega end groups of the polymer; $R^1$ represents a hydrogen atom or a straight or branched chain alkyl group; $R^2$ represents a straight or branched chain alkyl group which is substituted by a group which may have a positive charge at physiological pH; and n represents the number of repetitive units of the polymer, or a copolymer thereof; for use as a medicament and for treatment of a heparin overdose wherein the polymer of formula (I) has been found to have a selectivity and affinity for heparin.

18 Claims, 10 Drawing Sheets

SEQUENCE LISTING

```
<160> NUMBER OF SEQ ID NOS: 2

<210> SEQ ID NO 1
<211> LENGTH: 4
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: benzene modification
<220> FEATURE:
<221> NAME/KEY: MOD_RES
<222> LOCATION: (2)..(2)
<223> OTHER INFORMATION: gamma OR modification
<220> FEATURE:
<221> NAME/KEY: MOD_RES
<222> LOCATION: (4)..(4)
<223> OTHER INFORMATION: pNA modification

<400> SEQUENCE: 1

Ile Glu Gly Arg
1

<210> SEQ ID NO 2
<211> LENGTH: 4
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: benzene modification
<220> FEATURE:
<221> NAME/KEY: MOD_RES
<222> LOCATION: (2)..(2)
<223> OTHER INFORMATION: gamma OR modification

<400> SEQUENCE: 2

Ile Glu Gly Arg
1
```

POLYMERIC SYNTHETIC ANTIDOTE

The present invention relates to a polymer substituted by a group which may have a positive charge when dispersed or dissolved in a medium at physiological pH for use as a medicament, particularly for treatment of a heparin overdose or for the neutralisation of heparin and a pharmaceutical composition comprising the polymer.

BACKGROUND OF THE INVENTION

Deep vein thrombosis, acute pulmonary embolism, myocardial infarction, unstable angina, arterial embolism, extra cerebral bleeding are various diseases requiring intravenous or subcutaneous heparin, either under acute or chronic way. Heparin administration is also indicated for the prevention of venous thrombosis that may arise during prolonged bed rest. This is true for patients with heart failure, or who have suffered from a heart attack or stroke. Patients subjected to major surgery, such as orthopaedic procedures as insertion of a prosthetic hip or knee, surgery involving cardiopulmonary bypass circuits, also benefit from treatment with UnFractionated Heparin (UFH).

In this clinical context UFH has been widely used for more than six decades thanks to its anticoagulant and antithrombotic activities. The mechanism of the anticoagulant action of this heparin has been extensively studied and largely explained. It acts by binding to antithrombin III present in blood plasma and by forming a complex that inhibits thrombin and coagulation factors IXa, Xa, and XIa. Structure and chemical properties of UFH have been elucidated in detail. It is a sulfated glycosaminoglycan composed of macromolecules with a molecular weight varying from 3,000 to 30,000 Da. When administered intravenously, UFH shows complex pharmacokinetics with anticoagulant action which cannot be precisely predicted and which differs considerably among patients. The dose-response relationship for UFH is nonlinear. Also, patient's response depends upon several factors such as: age, gender, body weight, smoking status, and renal function. As a consequence in clinical practice, it is very difficult to achieve a precise control of the therapeutic anticoagulation. UFH overdoses are therefore not rare in clinic. Administration of UFH requires a close monitoring of hemostasis via analysis of activated partial thromboplastin time (aPTT) or a specific dosage of factor Xa/IIa. Although well tolerated in most cases, the administration of UFH can lead to various side effects, such as haemorrhage, thrombocytopenia and osteoporosis. In the mid-1980s low-molecular-weight heparins (LMWH) were introduced in clinic practice as antithrombotic drugs first to prevent postoperative deep vein thrombosis. LMWHs have molecular weights ranging from 2,000 to 10,000 Da. Recent studies have highlighted that LMWHs cause fewer side effects, although, at the same time, demonstrating low pharmacological potency compared to UFH.

In contrast to some chronic side effects of heparin, haemorrhage requires the rapid neutralization of heparin by the administration of an antidote. Until now protamine sulfate (PS) is the only drug available on the market to counteract quickly and efficiently the action of heparin. The European Pharmacopoeia monograph defines protamine sulphate as consisting of the sulphate of basic peptides extracted from the sperm or roe of fish, usually species of Salmonidae and Clupeidae. Upon injection within blood PS forms stable polyelectrolyte complexes with heparin and reverses its anticoagulant activity.

A disadvantage of PS arises from its natural origin which causes several limitations on the final characteristics of the product, such as a lack of control of its molecular features (primary amino sequence, molecular weight). For example when subjected to reversed phase high performance liquid chromatography (RP-HPLC) salmon protamine appears as a mixture comprising four main components accompanied by a number of minor species. This purity level, but also its natural source represents therefore a potent risk of persistence of residues, such as heavy metals, endotoxins and other antigenic biological contaminants.

The availability issue is a further disadvantage of PS, as indicated in a recent report of the European Medical Agency. Indeed with the recent fishing restrictions in Japan following the earthquake and the tsunami in March 2011, sourcing of the raw material was done in other fishing grounds and the new natural raw material has shown endogenous heterogeneity. The European Medical Agency was informed by member states, as well as from market authorisation holders that a potential supply shortage of the protamine sulphate containing medicinal products may occur shortly.

There have been research efforts to identify potential alternatives to protamine sulfate. For example salicylamide derivatives, water-soluble chitosan, or low molecular weight protamine have been tested. However, no compound other than PS is currently admitted in clinic to neutralize heparin. The literature has not reported a drug more potent and safer than protamine. Heparinase for example after clinical trials has proved to be more risky than PS.

In US2012308546, J. N. Kizhakkedathu et al. reported the neutralization of heparin (UFH and LMWH) with synthetic polymers consisting in a hyperbranched polyglycerol core grafted with polyvalent primary amino-groups. However, these polymers are complex macromolecular structures which require several tedious steps for their synthesis. Moreover, high molecular weight polymers may have poor clearance capability.

In JP 2012 029831 and in "Bioconjugate Chemistry, vol 22, p 193", Yasuhide et al. reported a heparin coating comprising a six-branched, star-shaped poly(2-(dimethylaminoethyl)-methacrylate) which provides antithrombogenicity. In that case, the synthetic polymer material is only used to fix heparin to the surface of a medical device in order to form a coating. With this coating, the antithrombogenicity of heparin is maintained and conferred to the surface.

Other synthetic polymers bearing amino groups such as polyethylene imine (PEI) and Polybrene have also been tested as heparin antidotes but the properties of these synthetic polycations are not favourable for pharmaceutical application. In particular, PEI has an extensive branched structure resulting in a compact structure which does not promote interaction with heparin.

BRIEF SUMMARY OF THE INVENTION

A way of ameliorating these problems has been sought.
According to the invention there is provided a polymer of formula (I):

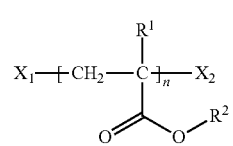

where $X_1$ and $X_2$ respectively represent the alpha and omega end groups of the polymer;

$R^1$ represents a hydrogen atom or a straight or branched chain alkyl group, preferably a straight or branched chain alkyl group comprising from 1 to 6 carbon atoms, for example a methyl group;

$R^2$ represents a straight or branched chain alkyl group which is substituted by a group which may have a positive charge at a physiological pH; and n represents the number of repetitive units of the polymer; or a copolymer thereof;

for use as a medicament.

According to the invention there is further provided a polymer of formula (I) as defined above for use in the treatment of a heparin overdose or for the neutralisation of anticoagulation.

According to the invention there is also provided a pharmaceutical composition comprising a polymer of formula (I) as defined above and a pharmaceutically acceptable diluent.

According to the invention there is further provided a pharmaceutical composition comprising a polymer of formula (I) as defined above and a pharmaceutically acceptable diluent for use as a medicament, particularly for use in the treatment of a heparin overdose or for the neutralisation of anticoagulation.

According to the invention there is also provided a method of treating a heparin overdose or for neutralising anticoagulation which method comprises a step of administering to a human or animal in need of such treatment an effective amount of a polymer of formula (I) as defined above.

It has surprisingly been found that a hemocompatible polymer of formula (I) as defined above has high affinity and selectivity for heparins including in complex biological medium such as human plasma and can be used as a novel efficient antidote of heparin. An advantage of the polymer of formula (I) is that it has an extended structure, with a flexible polymer backbone which overcomes the problem with PEI that has a compact structure. The polymer of formula (I) has a chemical structure which promotes interaction with heparins, in particular their low molecular species (LMWHs). A further advantage of the polymer of formula (I) is that non-specific interactions with cellular and humoral compounds present in plasma are limited, in particular with negative charges present on the surface of blood cells and several plasma proteins, such as albumin, fibrinogen, but also several proteins involved in the biological cascade of the coagulation and with the stimulation of the complement system.

In some embodiments, the polymer of formula (I) may have a mean pKa of from 6 to 8, for example a pKa which is around physiological pH which is about 7.4. An advantage of this embodiment is that it ameliorates a problem with PEI which is that branched PEI has a pKa value of from 8.2 to 9.9 which in combination with its molecular weight (Mw) and branching level, results in a too high charge density of positive groups which is believed to cause cytotoxicity.

It is well known by a person of skill in the art that the alpha and omega groups represented by $X_1$ and $X_2$ are affected by the nature of the reaction conditions used for synthesis of the polymer of formula (I) such as the initiator, nature of co-monomers, if present, and conditions of polymerisation termination. In some embodiments, the polymer of formula (I) may be formed by radical polymerisation, and in particular by atom-transfer radical polymerization (ATRP) in which these factors are well known according to the state of the art. In some embodiments, where a co-monomer is not present, $X_1$ may represent an ethyl isobutyrate moiety and $X_2$ may represent a hydroxyl group.

In some embodiments, $R^2$ represents a straight or branched chain alkyl group comprising from 1 to 10 carbon atoms, preferably from 1 to 6 carbon atoms, for example two carbon atoms. Optionally the group which may have a positive charge at physiological pH is a group of formula —N($R^3$)$_2$ (II) wherein $R^3$ may be the same or different and represents a hydrogen atom or a straight or branched chain alkyl group. In some embodiments, the substituent $R^3$ may represent a straight or branched chain alkyl group to improve hemocompatibility. In some embodiments, the straight or branched chain alkyl group represented by $R^3$ may have from 1 to 6 carbon atoms, for example from 1 to 4 carbon atoms, particularly $R^3$ may represent a methyl group.

In some embodiments, the polymer of formula (I) has a mean charge density which is the proportion of the number of positively charged repetitive units to n, the number of repetitive units. A positively charged repetitive unit is a repetitive unit of the polymer of formula (I) which has an $R^2$ substituent which represents a straight or branched chain alkyl group which is substituted by a group which has a positive charge, for example a protonated group of formula (II) or a group of formula —NH($R^3$)$_2^+$ (III). The protonated group of formula (II) may be formed when the polymer of formula (I) is dispersed or dissolved in a physiologically compatible medium such as an isotonic saline solution or phosphate buffer saline medium (PBS). The group of formula (III) may be formed during the preparation of the polymer, for example during a purification step in a basic solution. In some embodiments, the mean charge density may be from 1, preferably from 20 to 80%, preferably to 50%. Most preferably, the polymer of formula (I) has a mean charge density from 15 to 30%.

The polymer of formula (I) is shown as not having a positive charge. In some embodiments, particularly when the polymer is dissolved or dispersed in a medium or solution at physiological pH, the polymer used in the invention may be a polymer of formula (IV):

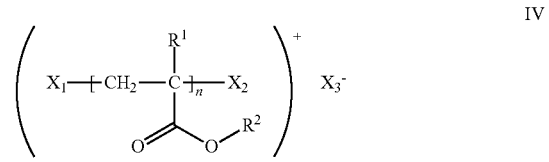

IV where $X_1$, $X_2$, $R^1$, $R^2$ and n are as defined above; and $X_3$ represents an anion, for example OH$^-$, Cl$^-$; HCO$_3^-$; NO$_3^-$; H$_2$PO$_4^-$. By co-polymer is meant a polymer comprising two or more repetitive units where the repetitive units can be organized according to a different architecture (for example linear, cyclic, grafted and/or star), sequence (for example random, block copolymer and/or micro-sequence), and/or configuration (for example atactic, isotactic and/or syndiotactic). The composition of the polymer of formula (I) may be altered by copolymerisation of monomers bearing positive charges but also non-ionic or/and anionic groups. The length of the polymer of formula (I) may also be adapted between some hundred to several thousands of Da, as required.

In some embodiments, the polymer of formula (I) may be a copolymer in order to modify the charge density of the polymer of formula (I) and to limit protein adsorption. The polymer of formula (I) has a repetitive unit of formula (V): —(CH$_2$—C(R$^1$)(C(O)OR$^2$))—. In some embodiments, the repetitive unit may be copolymerised with one or more of the following repetitive units: an ethylene glycol, an acrylate, a methacrylate, optionally carrying a polyethylene oxide (PEO), preferably with a mean Mw typically from 400 to 5,000, or a repetitive unit of formula (VI) which is —(CH$_2$—C(R$^1$)(C(O)OR$^4$))— where R$^4$ represents a straight or branched chain alkyl group substituted by a group —N$^+$(R$^3$)$_3$ of formula (VII) where R$^3$ is as defined above. Although a random distribution of this co-monomer is preferred, a block-wise or multi-block structure can also be adopted. The straight or branched chain alkyl group R$^4$ may have from 1, for example from 2 to 10, for example to 6 carbon atoms, particularly R$^4$ may have two carbon atoms.

Examples of co-polymeric structures which could be used as the polymer of formula (I) include the following:

Copolymer of poly[2-(dimethylamino)ethyl methacrylate)-co-acrylic acid]:

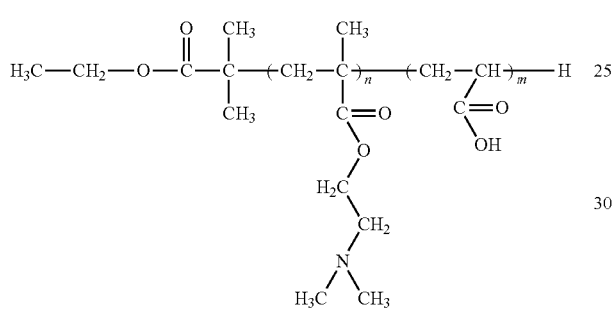

Copolymer of poly[2-(dimethylamino)ethyl methacrylate)-co-methacrylic acid]

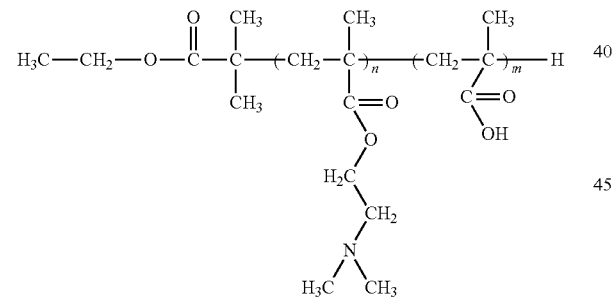

Copolymer of poly[2-(dimethylamino) ethyl methacrylate)-co-poly(ethylene glycol) α-methyl ether, ω-acrylate]:

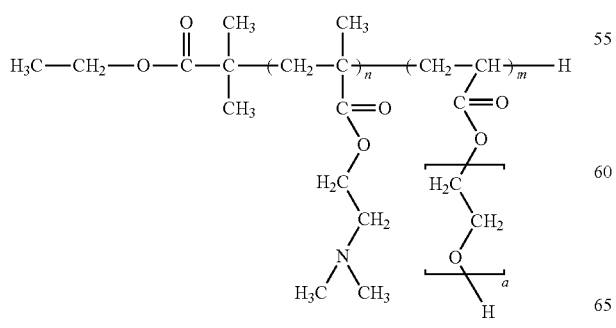

Copolymer of poly[2-(dimethylamino) ethyl methacrylate)-co-poly(ethylene glycol) α-methyl ether, ω-methacrylate]:

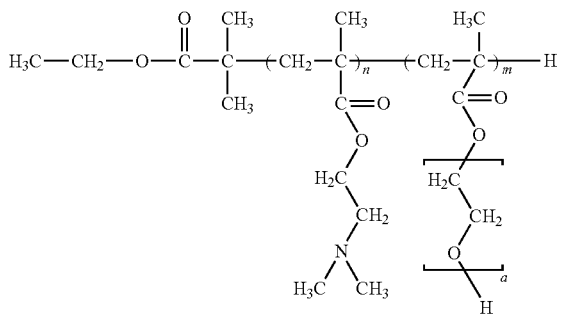

Copolymer of poly[2-(dimethylamino) ethyl methacrylate)-co-poly(ethylene glycol)]:

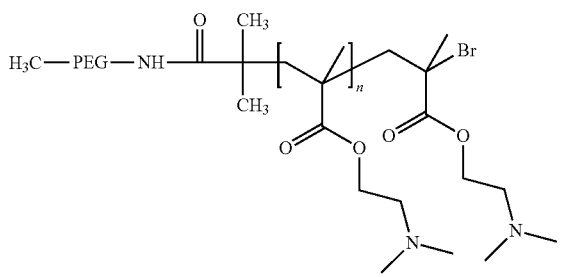

Copolymer of poly[2-(dimethylamino) ethyl methacrylate)-co-poly(ethylene glycol)]:

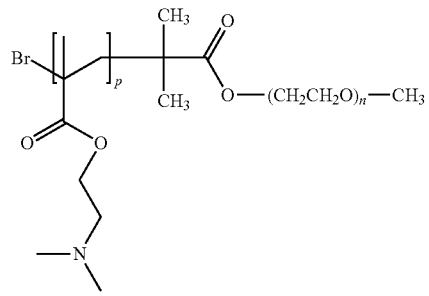

Terpolymer of poly[methacrylic acid-co-2-(dimethylamino) ethyl methacrylate)-co-poly(ethylene glycol) α-methyl ether, ω-methacrylate]:

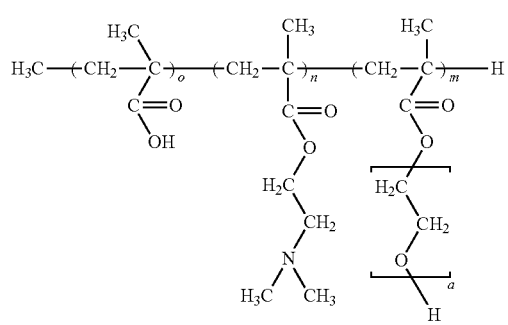

Terpolymer of poly[methyl methacrylate-co-2-(dimethylamino) ethyl methacrylate)-co-poly(ethylene glycol) α-methyl ether, ω-methacrylate]:

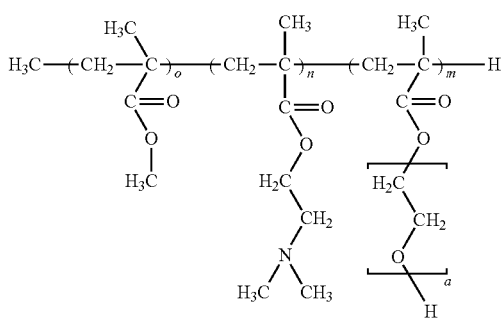

Terpolymer of poly[trimethylamino) ethyl methacrylate-co-2-(dimethylamino) ethyl methacrylate)-co-poly(ethylene glycol) α-methyl ether, ω-methacrylate]:

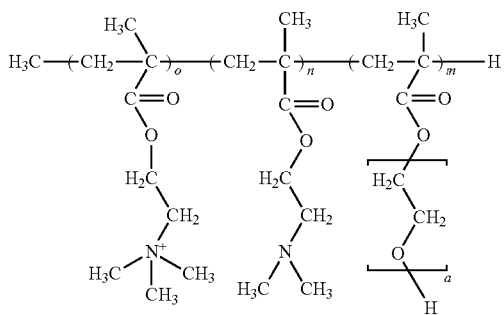

Copolymer of poly[trimethylamino) ethyl methacrylate-co-2-(dimethylamino) ethyl methacrylate]:

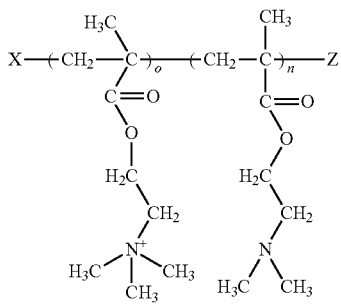

In some embodiments, the polymer of formula (I) may be a hemocompatible polymer. By hemocompatible it is meant that the polymer of formula (I) does not elicit a substantial adverse reaction when in contact with a patient's blood compartment. The criteria for hemocompatibility are detailed in ISO 10993-4 and include, for example, that there is substantially no hemolysis, no activation or inhibition of coagulation cascade, no complement activation and no cell activation aggregation (specifically for platelet).

In some embodiments, the polymer of formula (I), pharmaceutical composition or method according to the invention is for the treatment of a heparin overdose or for the neutralisation of anticoagulation. A typical clinical application where neutralisation of anticoagulation is required is where anticoagulation induced by heparin results in bleeding in a patient who had received heparin, a patient who has extracorporeal circulation (ECC), in particular for heart and aorta surgery, burns, atrial fibrillation, acute coronary syndrome, pancreatitis, kidney filtration, cancer chemotherapy and/or cardiac bypass. In other clinical situations an excess amount of heparin may have to be neutralized following the maintenance of an intravenous catheter or any other hospital or medical systems placed in contact with the blood compartment.

In some embodiments, the polymer of formula (I), pharmaceutical composition or method according to the invention is for treatment of a patient requiring reversal of heparin action, for example in a case of bleeding during percutaneous vascular surgery in particular for neurovascular interventions.

Unless otherwise defined, the molecular weight (Mw or Mn) or molecular mass is expressed in Daltons (Da). In some embodiments, the polymer of formula (I) may have a linear structure, particularly of the family of poly(meth) acrylates. In some embodiments, n represents an integer which may have a value of from 6 to 130 such that the polymer of formula (I) may have a molecular weight of from 1,000, preferably from 2,000 to 20,000, preferably to 15,000. Most preferably, the polymer of formula (I) has a molecular weight between 4,000 and 10,000.

The polymer of formula (I) offers several advantages over naturally occurring polycations. In particular due to their synthetic origin their macromolecular features can be adapted in a versatile way. For example their mean charge density and charge distribution can be easily modified by using at least substituted and unsubstituted repetitive units whose molar proportion and distribution within the polymer of formula (I) may be random or can be tailored to control the interaction of the polymer of formula (I) with a defined polyanion such as heparin.

In some embodiments, the polymer of formula (I) may comprise a substituted repetitive unit comprising N,N dimethyl amino ethyl methacrylate (such that the polymer is PolyDimethyl Amino Ethyl MethAcrylate or PDMAEMA). PDMAEMA has a mean charge density of about 30%.

With an exponential factor of the Mark-Houwink parameters of 0.5 and 0.6, linear PDMAEMA has a relatively high expanded conformation, a macromolecular feature allowing the interaction with heparin. With a mean pKa of around physiological pH which is about 7.4, PDMAEMA has a relatively low mean charge density compared to PEI or poly(L)Lysine. Accordingly its hemocompatibility and cytotoxicity is superior compared to polycations bearing too many positive charges on their backbone.

Based on investigations carried out in vitro, it has surprisingly been found that low molecular weight PDMAEMA is able to rapidly form polyelectrolyte complexes (PEC) with heparin both in a saline medium buffered at pH 7.4 and in more complex medium such as human plasma.

In a saline medium the kinetics of this physico-chemical interaction proceeds rapidly, achieving a steady state in a range of some minutes with the production of stable nanoparticles of a mean size around 250 nm. These complexes have been found to be stable at least for 24 hours at 37° C. in phosphate buffered saline medium (PBS). According to the invention, there is further provided a polyelectrolyte complex of a polymer of formula (I) with heparin. In some embodiments, the polyelectrolyte complex may have a homogeneous size distribution, for example the polyelectrolyte complex may have a mean radius below 500 nm, for example the polyelectrolyte complex may have a mean radius of from 5 to 130 nm. The polyelectrolyte complex is a stable complex for at least five minutes or for at least two hours or for at least 24 hours. In some embodiments, heparin may refer to a medication which has an anticoagulant effect which has the structure of the whole or of an active part of heparin, for example unfractionated heparin or to a low molecular weight heparin. Examples of low molecular weight heparin include bemiparin, calcilean, calciparine, certoparin, dalteparin, enoxaparin, hepalean, heparin, heparin leo, liquaemin, choay heparin, nadroparin, parnaparin, reviparin and/or tinzaparin.

In human plasma both the coagulation bioassay (also called "activated partial thromboplastin time" or aPTT bioassay) and the remaining activity of anticoagulation factor Xa show the specificity of the interaction of these synthetic polymers of formula (I) with heparins leading to a nearly entire reversal of the anticoagulation action of UFH and up to 54% of the action of LMWH.

A dose response curve carried out in human plasma also reveals the high affinity of PDMAEMA for UFH allowing to successfully neutralize UFH in a similar concentration range as protamine, the natural antidote which is the only one available on the market.

The selectivity and affinity of the polymer of formula (I) to both forms of heparin in a highly complex medium as human plasma is surprising taking into account the presence of numerous proteins mostly negatively charged at physiological pH and present at a concentration up to 40,000 higher than heparin.

By comparison, the action of another synthetic polycation, Polybrene, has been found to be less effective than the polymer of formula (I).

In whole human blood, the polymer of formula (I) for heparin neutralization has also surprisingly revealed efficiency and effectiveness. Dose-response curves carried out in whole human blood reveal the high affinity of polymers of formula (I) for UFH allowing to successfully neutralize UFH with a higher efficiency compared to protamine.

By comparison with UFH neutralization assay done in human plasma, the presence of blood cells, particularly red blood cells and platelets which are highly concentrated in blood and well-known to be negatively charged, do not interfere significantly with the pharmacological activity of the polymer of formula (I). The optimal weight ratio between UFH and the polymer of formula (I) to mostly inhibit anticoagulation activity is around 1 to 1.3.

As additional advantages, the polymer of formula (I) is easy to produce at an industrial scale and at a very low cost. Its macromolecular characteristics and purity can be easily controlled by macromolecular engineering which allows the adjustment of their composition, length, and sequence.

In some embodiments, the polymer of formula (I) may be in lyophilisate form. A skilled person would know how to prepare a suitable lyophilisate form of the polymer of formula (I). The lyophilisate form of the polymer of formula (I) could be reconstituted in a buffered isotonic medium just before injection.

In some embodiments, the pharmaceutical composition according to the invention may be an isotonic solution, for example a sterile isotonic solution which is optionally buffered at pH 7.4. The diluent may be an optionally buffered isotonic medium, for example a phosphate buffered saline medium (PBS). A suitable PBS composition is for example: composition: $KH_2PO_4$: 1.4 mM $Na_2HPO_4$ 10 mM NaCl 137 mM, KCl 2.7 mM and adjusted to pH 7.4. A skilled person would know how to prepare a suitable optionally buffered, sterile isotonic solution of the polymer of formula (I). The pharmaceutical composition may have a concentration of the polymer of formula (I) of from 0.2 and 2 mg/mL. The concentration of the polymer of formula (I) in the pharmaceutical composition according to the invention may be from 10 to 1000 times higher than the final concentration to be achieved in whole blood.

BRIEF DESCRIPTION OF THE DRAWINGS

The invention will now be illustrated with reference to the following figures of the drawings which are not intended to limit the scope of the invention claimed.

DETAILED DESCRIPTION OF THE INVENTION

Figure 1:
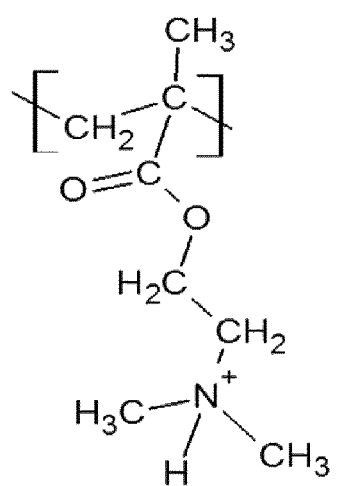
FIG. 1 shows the general structure of a repeating unit of PDMAEMA dispersed or dissolved in a medium at physiological pH.

FIG. 1 shows the general structure of a repeating unit of PDMAEMA dispersed or dissolved in a medium at physiological pH.

Figure 2A:
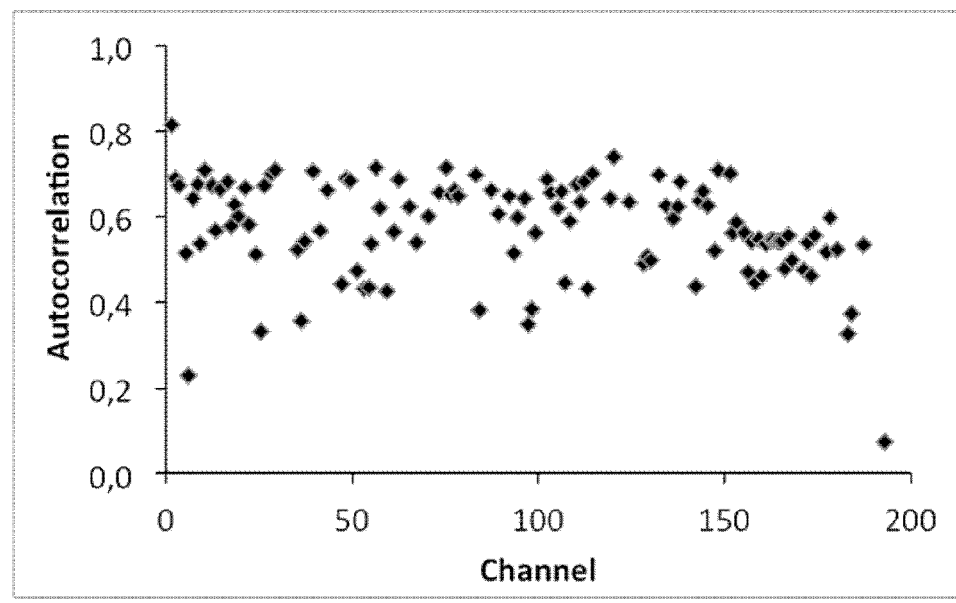
FIG. 2 shows dynamic light scattering (DLS) signal of a solution of a polymer of formula (I) before (A) and after addition of heparin (B) where the grey line is a replicate.

FIG. 2 shows the evolution of the dynamic light scattering (DLS) signal (duplicate) of a solution of a polymer of formula (I) before (A) and after addition of heparin (B).

Figure 3A:
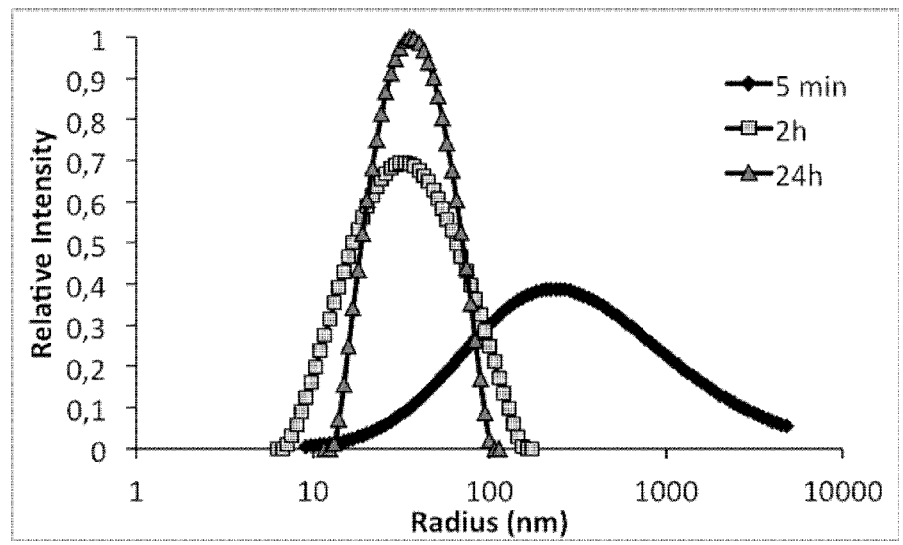
FIG. 3 shows size distribution of polyelectrolyte complexes at 5 minutes, 2 hours and 24 hours after mixing UFH and protamine (A), sample CLC1 (B), or sample CLC2 (C)
Figure 3B:
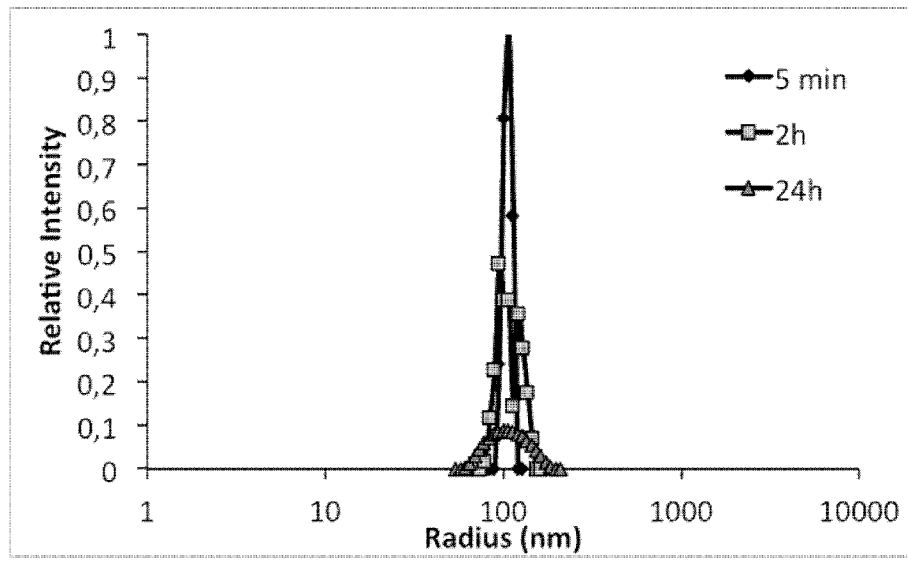
Figure 3C:
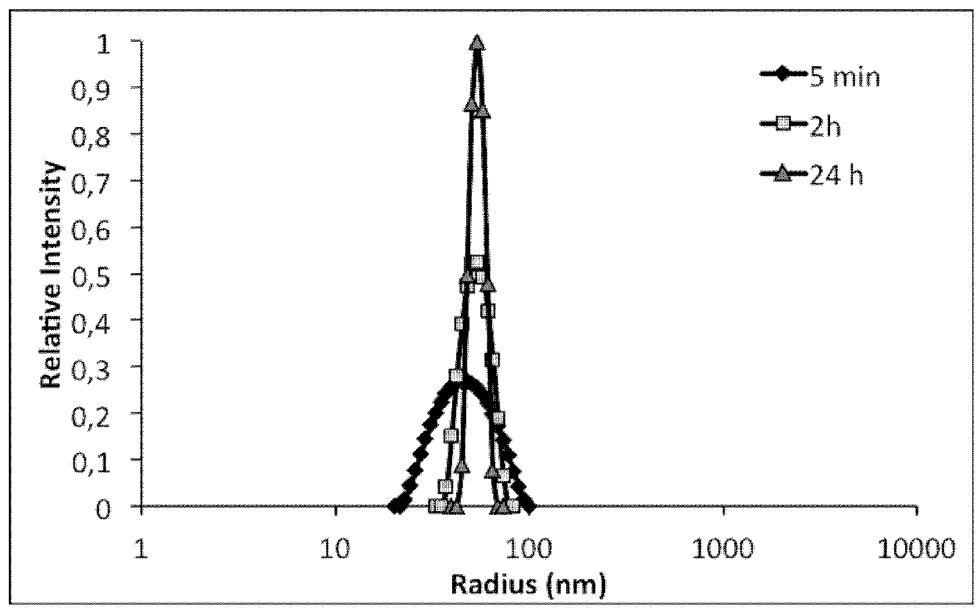

FIG. 3 shows the evolution of the size distribution of polyelectrolyte complexes (PECS) 5 minutes, 2 hours or 24 hours after mixing UFH and protamine (A), CLC1 (B), or CLC2 (C) in a PBS medium at 37° C. The final concentration of heparin and polymers of formula (I) are respectively 8 and 10 µg/mL.

Figure 4:
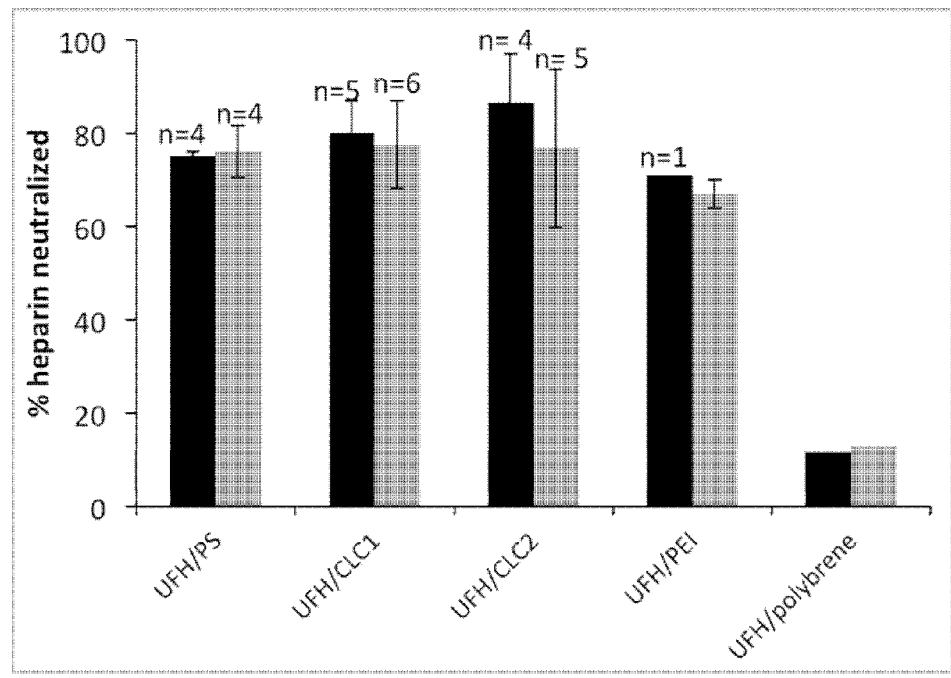
FIG. 4 shows percentage of neutralization of UFH by protamine, sample CLC1, sample CLC2, PEI and Polybrene in plasma previously spiked with UFH (2 µg/mL) for two groups of donors (black bars: average age of 22 years and grey bars: average age of 52 years)

FIG. 4 shows a comparison of the percentage of neutralization of UFH by protamine, CLC1, CLC2, PEI (10 KDa) and Polybrene (2 μg/mL) in plasma previously spiked with (UFH (2 μg/mL). An incubation of 15 minutes at 37° C. has been respected before measuring the neutralization. The percentage of heparin neutralization has been calculated adopting two different calibration curves of heparin in function of the group age of the donors (black and grey bars). The statistical tests (Anova Test and Tukey Kramer HSD) have not highlighted significant differences between the different groups (p>0.05).

Figure 5:
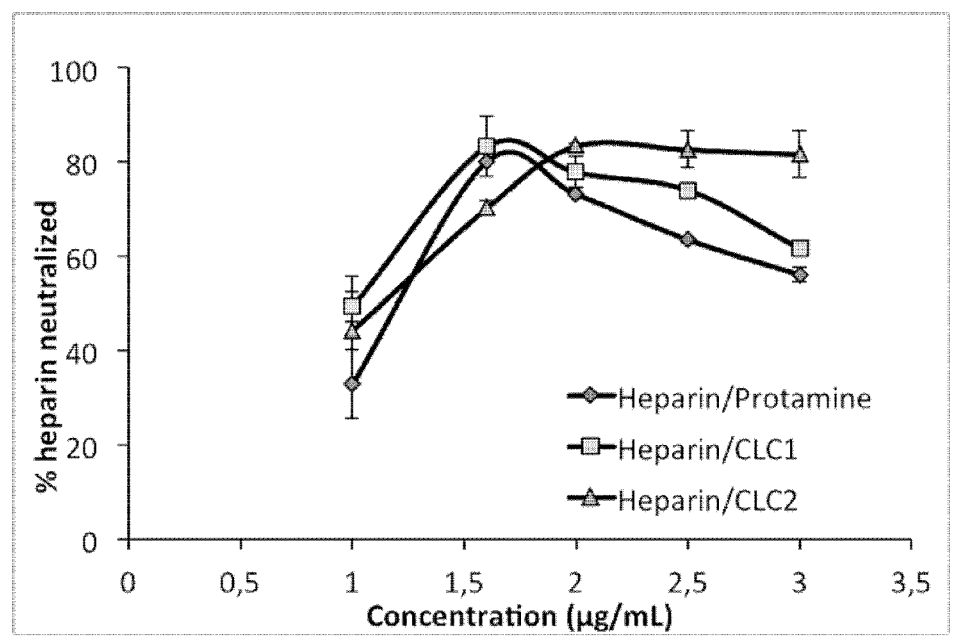
FIG. 5 shows dose-response curves of protamine, sample CLC1 and sample CLC2 versus neutralized fraction of UFH using aPPT bioassay. The mean and standard deviations are calculated from two independent experiments performed on senior blood donors.

FIG. 5 shows dose-response curves of polymer of formula (I) (Protamine—CLC1 or CLC2) versus neutralized fraction of UFH in human blood plasma adopting aPPT bioassay. The mean and standard deviations have been calculated from two independent experiments performed on senior blood donors.

Figure 6:
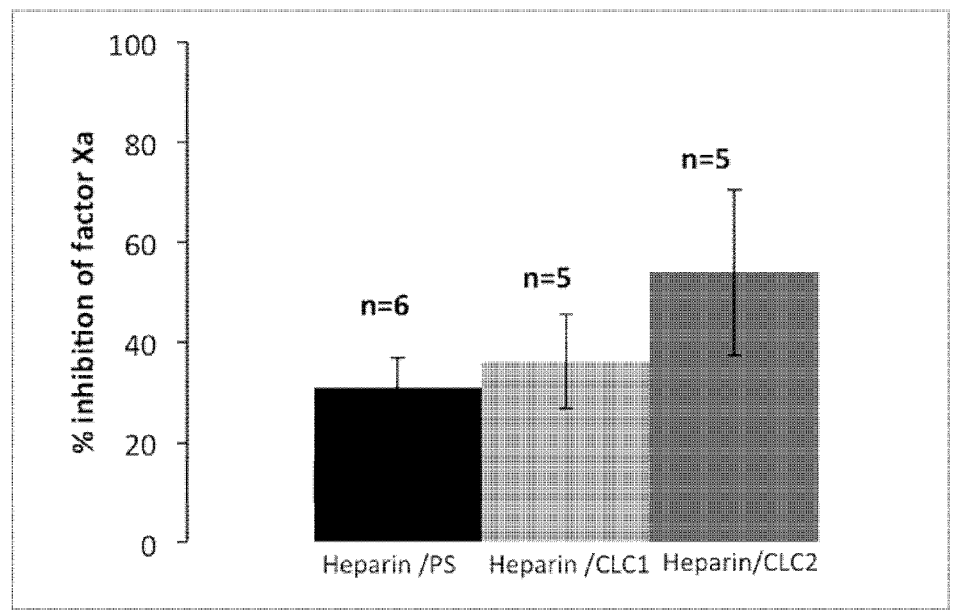
FIG. 6 shows percentages of inhibition of factor Xa by the polymers of formula (I) in comparison to protamine.

FIG. 6 shows percentages of inhibition of factor Xa by the polymers of formula (I) in comparison to protamine. LMWH and protamine were added at a concentration of 0.4 μg/mL each. The human plasma incubation was incubated for 15 minutes at 37° C. before analyzing the activity of factor Xa adopting the chromogenic test: Kit Coatest Heparin from Instrumentation Laboratory. The Anova Test and Tukey Kramer HSD did not highlight any significant difference between protamine and the two synthetic polymers of formula (I) (p>0.05).

FIGS. 7 to 10 show dose-response curves of different polymers and co-polymers of formula (I) versus neutralization fraction of UFH using aPPT bioassay. The efficiency and effectiveness of heparin neutralization were evaluated in whole human blood.

Figure 11:
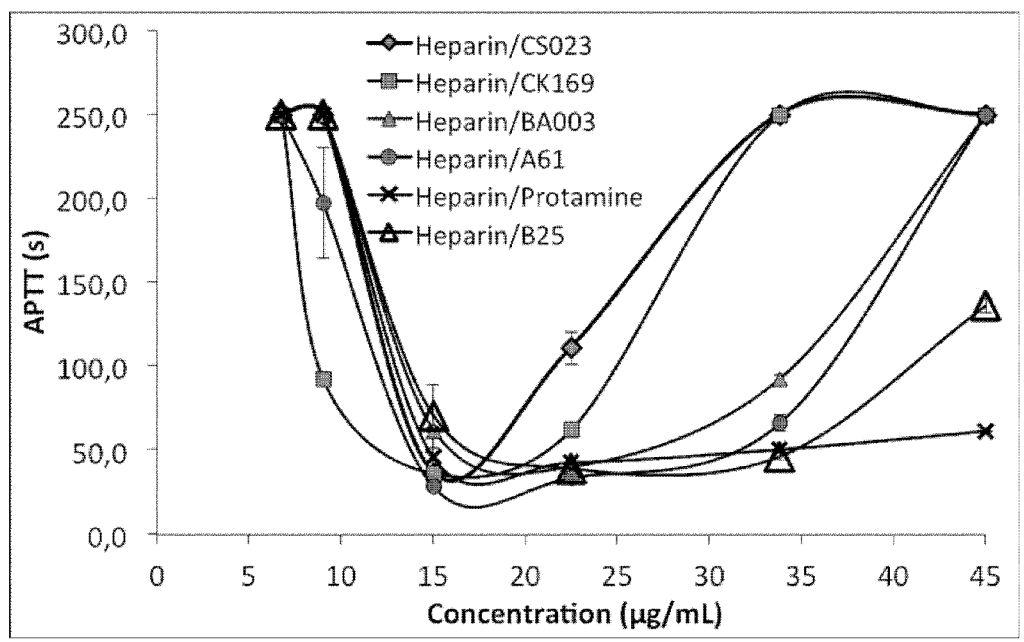
FIG. 11 shows dose-response curves of samples CS023, CK169, BA003, A61 and protamine versus neutralized fraction of UFH using aPTT bioassay.

FIG. 11 shows dose-response curves of different polymers and co-polymers of formula (I) versus neutralization fraction of UFH using aPTT bioassay. UFH was injected in human patients subjected to extracorporeal circulation during a cardiovascular surgical operation.

The invention will now be illustrated with reference to the following Examples which are not intended to limit the scope of the invention claimed.

EXAMPLES

Materials 2-(dimethylamino) ethyl methacrylate (DMAEMA) and unfractioned heparin (UFH) (porcine intestinal mucosa, grade 1-A, ref: H3393-25KU>170 U/mg) were purchased from Sigma. Branched PEI, Mw 10,000, was from Polysciences Europe (Eppelheim, Germany). Two protamine batches were originated either from Sigma (solid form, grade X, ref: P4020-1G), or from Leo Pharma (solution form, ref: 0072439). Injectable solution of heparin was from Leo Pharma (100 IU/mL ref: 1406453). The low molecular weight heparin, Clexane/enoxaparin (80 mg/0.8 mL) was from Sanofi Aventis, ref: 0278192). STA*-C.K. Prest*2 kit (kaolin, for determination of the activated partial thromboplastin time aPTT) was provided by Diagnostica Stago (AsniBrès sur Seine, France). All other chemicals and reagents used were of analytical grade. Phosphate buffered saline (PBS), pH 7.4 was composed from $KH_2PO_4$, 1.4 mM; $Na_2HPO_4$, 10 mM; NaCl, 137 mM; and KCl, 2.7 mM.

Synthesis, Characterization and Purification of Poly(Dimethyl Amino Ethyl MethAcrylate Poly(Dimethyl Amino Ethyl MethAcrylate (PDMAEMA) was synthesised by solvent-free, atom-transfer radical polymerization (ATRP) [S. Pirotton, C. Muller, N. Pantoustler, F. Botteman, S. Collinet, C. Grandfils, G. Dandrifosse, P. Degée, P. Dubois, M. Roes, *Enhancement of transfection efficiency through rapid and noncovalent post-PEGylation of poly(dimethylaminoethyl methacrylate)/DNA complexes*, Pharm. Res. 21 (2004) 1471-1479]. After polymerization, the polymer was purified in three successive steps consisting of chromatography realized on alumina support, precipitation in heptane, and dialysis against MilliQ (1MΩ·cm) water, using a cellulose membrane (cut-off 10,000). The purified polymer was dried by lyophilization. Relative average Mn and Mw were determined by size exclusion chromatography in THF/triethylamine (TEA) (2.5%) against polystyrene standards. The composition and purity of PDMAEMA were verified by $^1H$ NMR spectroscopy in $CDCl_3$.

According to this procedure, two PDMAEMA samples of different molecular weights were synthesised, purified and characterised. Their relative number-average molecular weight (Mn) was 8,000 (code CLC1) and 15,000 (code CLC2).

Blood Sample Collection

Human blood was obtained from the Red Cross Transfusion, Central Hospital, University of Liège. Blood was collected from healthy donors in 4.5 mL tubes containing 3.2% sodium citrate. Experiments were done within 2 hours after collection. This study received the approval of the Ethics Committee of the University hospital of Liège.

Kinetics Study of the Formation of Polyelectrolyte Complexes in PBS by Dynamic Light Scattering All solutions of polyelectrolyte complexes (PECs) were pre-equilibrated at 37° C. and at the concentration required (between 5-10 μg/mL) at least 15 minutes prior to the analysis.

For the PECs formation, heparin was first added before the PBS. 5 minutes later the polymer of formula (I) was added to the mixing. Homogenization was realized by 3 up-and-down movements.

Formation of polyelectrolyte complexes was monitored by dynamic light-scattering (DLS) at 37° C. during at least two hours (DLS equipment Photocor Corporation U.S.). The mean light scattering intensity at 90° was analysed as well as the evolution of the autocorrelation signal.

Anticoagulant Activity Assays

Activated partial thromboplastin time (aPTT) and anti-Xa activity were measured on the freshly isolated plasma using respectively a coagulometer (BCT; Dade Behring—Siemens) and a Microplate reader (Anthos HT3, type 12600). STA-C.K. Prest*2 kit was used. Coatest kit was used to evaluate the concentration of low molecular weight heparin in blood plasma following the reactions depicted below:

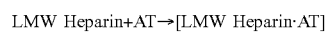
LMW Heparin+AT→[LMW Heparin·AT]

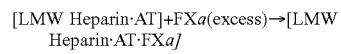
[LMW Heparin·AT]+FXa(excess)→[LMW Heparin·AT·FXa]     2a.

S-2222+FXa→Peptide+pNA (yellow)+FXa(residual)     2b.

Where FXa represents factor Xa and S-2222 represents Bz-Ile-Glu-(γ-OR)-Gly-Arg-pNA (CA: 59068-47-2) (SEQ ID No. 1), a chromogenic substrate cleaved by free FXa to peptide (Bz-Ile-Glu-(γ-OR)-Gly-Arg (SEQ ID No. 2)) and pNA (p-nitroaniline). AT represents antithrombin. Heparin binds to AT, causing a change in the conformation of AT to a form that binds to and sequesters the activity of FXa. Addition of a peptide that competes with AT for heparin will increase the concentration of free FXa. Thus, restoration of the activity of FXa, as indicated by the amount of S-2222 converted to peptide and pNA, provides a measure of the ability of a peptide to neutralize the anticoagulant activity of heparin (provided in technical sheet of Instrumentation Laboratory).

The assay method was calibrated using standard solutions that contain 0.1 µg/mL of AT and heparin at concentrations ranging from 0.01 to 0.07 µg/mL in buffer/normal human plasma supplied with the Coatest kit. The standard solutions were incubated at 37° C. for 3-4 minutes, after which 100 µL of bovine factor Xa (0.71 nkat) were added to 200 µL of each standard solution. The mixtures were incubated at 37° C. for 30 sec, after which 200 µL of S-2222 (0.2 µmol, 37° C.) were added and the reaction mixtures were incubated at 37° C. for exactly 3 minutes. Reaction was stopped by addition of 300 µL of 20% (vol/vol) acetic acid. The absorbance was measured at 405 nm. The ability of CLC1 and CLC2 to neutralize the anticoagulant activity of heparin was determined by addition of each polymer to heparin solution, and the assay performed as described above.

All PECs were prepared by addition of 100 µL of heparin (10 µg/mL) to 300 µL of plasma. After a pre-incubation of 5 minutes at 37° C., 100 µL of a stock solution of polymers of formula (I) (10 µg/mL) was added to neutralize heparin. After 15 minutes of interaction 37° C. the aPTT analysis was performed. Anti Xa analysis was evaluated according to a similar procedure, except for the final concentrations of heparin and polymer of formula (I) which were 4 µg/mL.

Statistics

ANOVA Test and Tukey Kramer HSD Test were Used as Statistical Tests.

Example 1

Example 1 studied the formation of a polyelectrolyte complex (PEC) according to the invention in PBS medium.

A first study was performed in vitro to assess the ability of the polymers of formula (I) to neutralize heparin (UFH) under the form of polyelectrolyte complexes (PECs) in PBS medium. In practice the kinetics of this interaction was analysed with dynamic light scattering (DLS), an analytical technique which also allows determining the size and stability of the PECs at 37° C. For comparison, these observations are compared with the PECs formed in the presence of heparin and protamine.

Figure 2B:
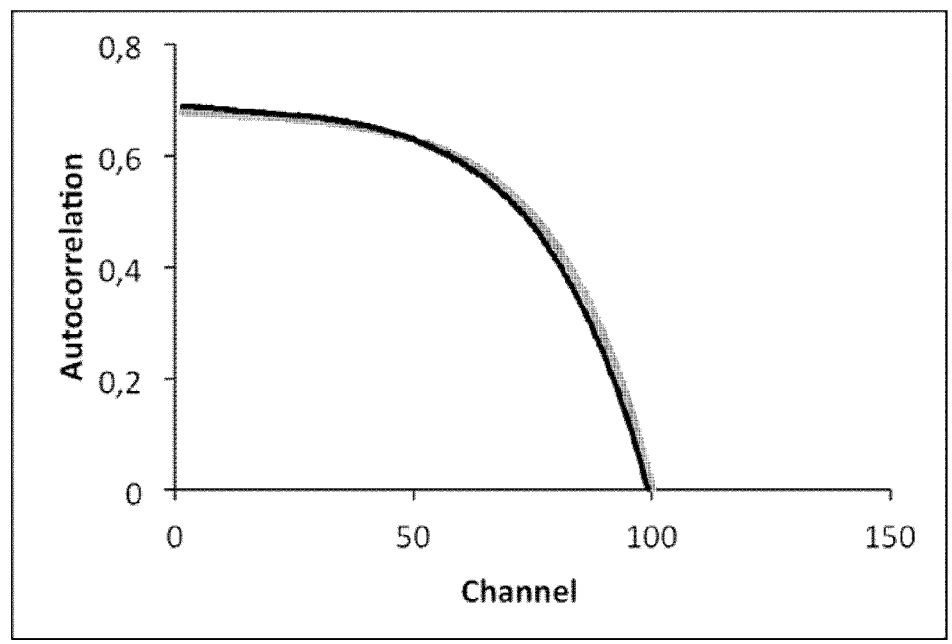

Upon mixing polymer of formula (I) solution with UFH, a change in the light scattering signal was observed by DLS. Indeed, from a cloud of points attesting from the absence of any correlation signal in the presence of a true polymer solution (FIG. 2A), the mixing of polymer of formula (I) and heparin solutions converts the DLS signal within some minutes in a regular exponential autocorrelation curve (FIG. 2B). This change in light scattering signals attests of the formation of nanoscale structures. Based on the time resolution of DLS, thus limited to a time scale in the minute range, one can at least state that the equilibrium in polyelectrolyte association is achieved within one to two minutes, although a more rapid constant rate of association cannot be ruled out.

The evolution of the size distribution of PECs at 5 minutes, 2 hours or 24 hours after mixing UFH and protamine (FIG. 3A), CLC1 (FIG. 3B), and CLC2 (FIG. 3C) in a PBS medium at 37° C. was analysed. The final concentrations of heparin and polymers of formula (I) are respectively 8 and 10 µg/mL. UFH and protamine result in broad curves, covering radii from 10 to over 1000 nm after 5 minutes and from about 10 to 100 nm after 2 and 24 hours. UFH and CLC1 and CLC2 result in quite broad curve after 5 minutes but in very narrow curves for longer times, with curves centred on about 100 nm for CLC1 and about 50 nm for CLC2. This indicates that the polymers of formula (I) (CLC1 and CLC2) show a greater stability after 2 and 24 hours than protamine. This phenomenon results in a smaller shift of the curves to the right part of the graph.

After deconvolution of these curves in view to determine the relative diffusion coefficient of these nanoparticles submitted to Brownian movement, the distribution size of the PECs is calculated adopting non-linear software. The comparison of the size distribution of the PECs given on FIG. 3 highlight another advantage of PECs made from our polymers of formula (I) compared to those made from protamine. Indeed if when initially made all PECs are in the nanosize range, thus with a mean radius of the complexes below 500 nm, the comparison of their size distribution clearly shows the polydispersity of the size of the PECs made from PS is up to 3 times wider than those made from our synthetic polymers of formula (I). Moreover when measured on a 24 hours period, a huge difference in PECs is noticed between protamine and CLC complexes. While the CLC complexes are relatively stable with a polydispersity which still decreases with time, on the contrary a significant aggregation occurs in the presence of PS complexes. Accordingly their mean size approaches the micron range with a polydispersity of particles ranging from 10 nm to more than 8 µm.

The results show that the PECs made from a compound according to the invention are homogeneous nano-size range particles in vitro in the experimental conditions adopted for this study and are dearly more stable compared to PECs made from PS.

Example 2

Example 2 was an in vitro study of the neutralization action of UFH by polymers of formula (I) in human plasma.

In view to assess the pharmacological activity of the polymers of formula (I) to neutralize the action of UFH, polymers of formula (I) were incubated in normal human plasma previously spiked with heparin, analysing afterwards the remaining coagulation activity of plasma using the activated partial thromboplastin time (aPTT) test. This bioassay was indeed typically used to analyse the functionality of the intrinsic pathway of the blood coagulation, using kaolin as synthetic activator of the coagulation. An incubation of 15 min at 37° C. was respected before measuring the aPPT test. The percentage of heparin neutralization in plasma (FIG. 4) was calculated using two different calibration curves of heparin in function of the group age of the donors. Indeed a difference in heparin sensitivity was noticed with aPPT test as a function of the range of age of human donors. Accordingly, two calibration curves of heparin were used, corresponding to the two categories of blood donors: group 1 (average age: 22 years) and group 2 (average age: 52 years). The statistical tests (Anova Test and Tukey Kramer HSD) did not highlight significant differences between the different groups (p>0.05).

As depicted on FIG. 4, the percentage of neutralization of heparin 15 minutes after addition of the polymers of formula (I) was at least identical or slightly superior compared to the heparin/protamine adopted as a control (85% for CLC2 compared to 75% for protamine). If a slight increase in neutralization effectiveness was observed for CLC2 compared to protamine, the statistical analysis of the data (Anova Test and Tukey Kramer HSD) indicates that this difference is not significant (p>0.05).

Example 3

In Example 3 the efficiency of heparin neutralization of UFH was compared with other known synthetic polymers of formula (I).

The heparin neutralization effectiveness of CLC1 and CLC2 was compared with a branched polyethylene imine (PEI 10 KDa) and a polybrene (2 µg/mL) (FIG. 4). The aPPT response shows that PEI has a lower neutralization efficiency compared to PDMAEMA assessed (CLC2). Indeed at the concentration in UFH (4 µg/mL in plasma), the neutralization of heparin provided by PEI is 70% against 80% for CLC2. Also for comparison purposes, the neutralization efficiency of polybrene is very low with only 10% of UFH neutralized.

TABLE 1

| | Antidote | PS | CLC1 | CLC2 | PEI | Polybrene |
|---|---|---|---|---|---|---|
| Group 1 | Mean | 75.0 | 80.0 | 86.5 | 70.8 | 11.5 |
| | SD | 0.9 | 7.0 | 10.4 | | |
| Group 2 | Mean | 76.1 | 77.5 | 76.7 | 66.9 | 13.0 |
| | SD | 5.6 | 9.4 | 17.0 | 3.0 | |

The data in Table 2 are presented as an alternative to FIG. 4. The data show a comparison of the percentage of neutralization of UFH by protamine, CLC1, CLC2, PEI (10 KDa) and Polybrene (2 µg/mL) in plasma previously spiked with UFH (2 µg/m). An incubation time of 15 minutes at 37° C. was respected before measuring the neutralization. The percentage of heparin neutralization was calculated adopting two different calibration curves of heparin in function of the group age of the donors (Group 1 and Group 2). The statistical tests (Anova Test and Tukey Kramer HSD) have not highlighted significant differences between the different groups (p>0.05).

Example 4

In Example 4, the polymer of formula (I) dose-response curve for UFH neutralization was measured in human blood plasma using aPPT bioassay.

In view to assess a possible difference in affinity between polymers of formula (I) and heparin versus protamine/heparin, dose-response curves were established, corresponding to a progressive titration of heparin action by increasing concentration of the polymers of formula (I) with aPPT bioassay (FIG. 5). This in vitro study was conducted adopting a fixed plasma concentration of UFH of 2 µg/mL added before the incubation with the polymers of formula (I). The concentration of the polymers of formula (I) was varied from 1 to 3 µg/mL. The mean and standard deviations (SD) were calculated from two independent experiments performed on senior blood donors.

A classical dose-response study with an asymptotic profile is evidenced with CLC2. In contrast, the curves corresponding to the neutralization of heparin by protamine and CLC1 are characterized by a maximum around 1.6 µg/mL. This clearly highlights the advantage of CLC2, PDMAEMA with a molecular weight of 15,000, with a wider range therapeutic index to efficiently neutralize heparin.

The concentrations in protamine to neutralize heparin as observed in this study, thus from 1.6 to 2 µg/mL, correspond to the typical dose adopted in clinic, with roughly a weight ratio of 1/1 between heparin and protamine in whole blood.

Example 5

In Example 5 the neutralization of UFH heparin by the polymers of formula (I) was analysed, measuring factor Xa.

To further test the neutralization efficiency of heparin, the activity of the coagulation factor Xa was assessed. This test was a complementary method to show the pharmacological action of polymers of formula (I) and to highlight one of its possible antagonism binding sites, but it also allows assessing the inhibition capacity of polymers of formula (I) on low molecular weight heparin. Indeed, the latter does not affect significantly the aPPT test, due to the selectivity of action of LMWH on factor Xa without any action of factor IIa.

Percentages of inhibition of factor Xa by polymers of formula (I) in comparison to protamine are summarized in Table 2. UFH and protamine are added at a concentration of 0.4 µg/mL. The human plasma was incubated for 15 minutes at 37° C. before analysing the activity of factor Xa adopting the chromogenic test (Kit Coatest Heparin from Instrumentation Laboratory). From the experimental data obtained, it can be stated that the polymers of formula (I) inhibit nearly all the activity of factor Xa, an observation which therefore supports the aPPT test. As results of two independent experiments carried out on normal human plasma, the mean inhibition of factor Xa is 94.0% for protamine, compared to 93.8 and 100.0% for CLC1 and CLC2 respectively. CLC2 is therefore the more efficient antidote to heparin compared to protamine and CLC1 which is in agreement with the coagulation test presented above.

TABLE 2

| | Protamine | | CLC1 | | CLC2 | |
|---|---|---|---|---|---|---|
| Test number | mean | SD | mean | SD | mean | SD |
| 1 | 88.1 | 6.7 | 88.1 | 14.6 | 100.0 | 0.0 |
| 2 | 100.0 | 0.0 | 100.0 | 0.0 | 100.0 | 0.0 |
| mean | 94.0 | 8.4 | 93.8 | 8.7 | 100.0 | 0.0 |

Example 6

In Example 6, the neutralization of low molecular weight heparin (LMWH) by the polymers of formula (I) was analysed.

The complexation of the synthetic polymers of formula (I) with low molecular weight heparin (LMWH) was assessed in vitro in the same experimental conditions as for UFH, thus using a concentration of heparin and polymers of formula (I) of 0.4 µg/mL. After their incubation of 15 minutes at 37° C., the remaining activity of factor Xa is recorded with the chromogenic assay Coatest Heparin. As shown on FIG. 6, the percentage of inhibition of heparin is higher for the two synthetic polymers of formula (I) (54.0 and 36.2% for CLC2 and CLC1, respectively) then for protamine (31.0

TABLE 3

| Antidote | PS | CLC1 | CLC2 |
|---|---|---|---|
| Mean | 31.0 | 36.2 | 54.0 |
| SD | 6.0 | 9.4 | 16.5 |

The data in Table 3 are presented as an alternative to FIG. 6. The data show percentages of inhibition of factor Xa by the PDMAEMA in comparison to protamine. LMWH and protamine were added at a concentration of 0.4 μg/ml each. The human plasma incubation was incubated for 15 minutes at 37° C. before analyzing the activity of factor Xa adopting the chromogenic test: Kit Coatest Heparin from Instrumentation Laboratory. The Anova Test and Tukey Kramer HSD did not highlight any significant difference between protamine and the two samples of PDMAEMA (p>0.05).

Example 7

In this example, a composition according to the invention was prepared.

Firstly, 1 L of a PBS solution, 8.01 g of NaCl (Mw 58.44), 0.19 g of $KH_2PO_4$ (Mw: 136.09), 1.42 g of $Na_2HPO_4$, (Mw: 141.96), 0.20 g of KCl (Mw: 74.555) were dissolved at room temperature under gentle magnetic stirring in about 500 mL of purified and apyrogenic water. After entire dissolution of the salts, the solution is quantitatively transferred in a volumetric flask of 1 L. Upon homogeneization the pH and conductivity of the PBS solution is verified before carrying out its sterilisation with a steam autoclave. The PBS solution is finally stored in a suitable receptacle at 4° C.

To prepare 1 L of the polymer solution, 1.00 g of PDMAEMA was weighted and then dissolved in 100 mL of the PBS solution prepared according to the formulation given above. After 2 hours of dissolution at room temperature under gentle magnetic stirring, the solution was quantitatively transferred in a volumetric flask of 1 L. Upon homogeneization the pH and conductivity of the PBS solution were verified before carrying out its sterilisation with a steam autoclave. This polymer is finally stored in a suitable receptacle either in aliquotes of 50 mL at −20° C.

Example 8

In this example, in order to facilitate the handling and storage of the polymer of formula (I), a freeze dried form of the polymer of (I) was prepared.

An aqueous solution of PDMAEMA was prepared and the polymer solution was frozen at a temperature below −20° C. in a receptacle suitable for freeze-drying. The frozen solution was then lyophilised under sterile conditions for a duration of 2 days in order to lyophilise successfully 1 L of the polymer solution. The final formulation was then stored at −20° C.

Example 9

In Example 9 several (co-)polymers of formula (I) were tested for neutralization of UFH in whole blood. Dose-response curves were established adopting a fixed concentration of 2 μg/mL UFH added in whole blood collected on sodium citrate. Five minutes after this preconditioning step, UFH neutralization was conducted by adding one of the (co-)polymers listed in Table 4 to 6. The concentration of these polymers was varied from 0.5 to 4 μg/mL in—whole blood. A special care was taken during the addition of the (co-)polymer solution in view to assure a rapid and reproducible homogenization of this solution in whole blood (rapid injection of solution in whole blood, i.e. in less than 1 s), followed directly by 3 up-and-down aspirations to avoid any risk of local over-concentrations. The total dilution arising from the UHF and polymer solutions represents only 10% to avoid any interference with coagulation pathways.

After a 15 minutes incubation period performed at 37° C. under lateral agitation the aPTT test was carried out immediately afterwards in order to determine the residual UFH activity. Efficiency and effectiveness of the polymers to neutralize UFH were estimated from the determination of two parameters: $IC_{50}$ and $C_{Max}$ respectively. $IC_{50}$ corresponds to the polymer concentration leading to 50% of its maximal capacity to neutralize UFH, while $C_{Max}$ is the minimal polymer concentration giving rise to a saturation in UFH neutralization. The mean and standard deviations were calculated from two independent experiments performed on senior blood donors initially collected under sodium citrate.

The different polymers and co-polymers tested are listed in Table 4 to 6 and the chemical structures are represented in Scheme 1. All values are listed in Tables 4 to 6 and the corresponding curves are presented in FIGS. 7 to 10.

Scheme 1: Chemical structures of PEO-PDMAEMA (A, coded A33 and B17), PDMAEMA quaternized (B, coded B23, B24 and B25), PDMAEMA-g-MAPEO (C, coded JV051, A124 and B86) and and PDMAEMA-MMA-g-MAPEO (D, coded A92 and A95).

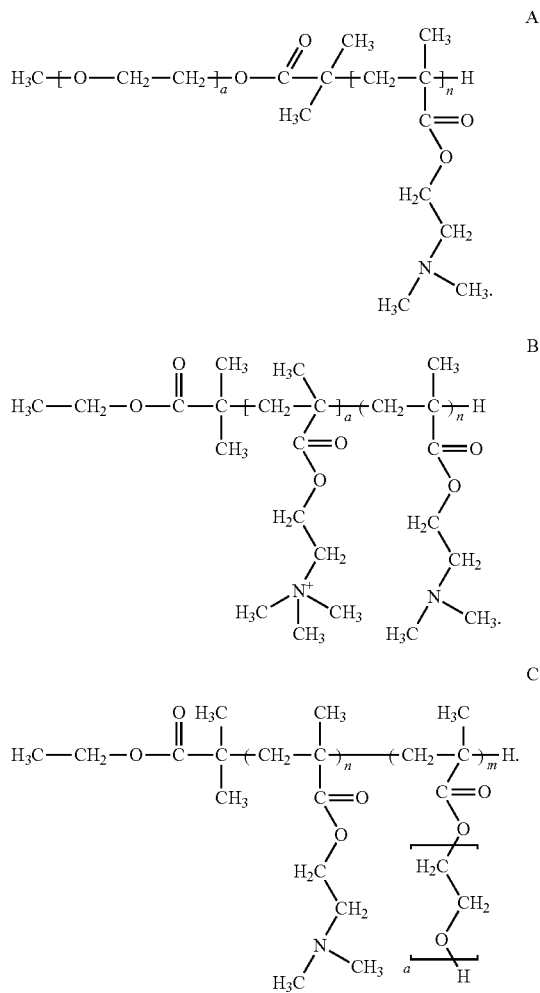

-continued

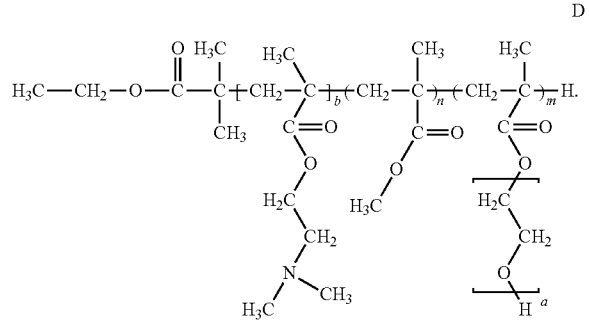

D

TABLE 4

| Code | Mn (co)polymer (g/mol) | Mn (PEO) (g/mol) | Structure | Proportion DMAEMA (wt %) | IC$_{50}$ (µg/mL) | C$_{Max}$ (µg/mL) |
|---|---|---|---|---|---|---|
| CS023 | 4,350 | — | Linear | 100 | 0.75 | 3.00 |
| B17 | 8,400 | 510 | Linear | 95 | 0.75 | 3.00 |
| CK169 | 10,100 | — | Linear | 100 | 0.60 | 1.60 |
| A33 | 14,200 | 510 | Linear | 98 | 0.55 | 1.60 |
| Protamine | 4,000 | — | Linear | — | 1.05 | 3.00 |

Affinity and selectivity of the heparin antidotes are the two main criteria to assess in view to identify the most potent (co-)polymers fitting to the clinical need. The former one will determine the total dose needed to neutralize a given amount of heparin administrated in the blood stream. If the latter one will also affect the global dose requested, it will also largely contribute to any side effects originating from the interaction of the drug with other biological sites than the targeted one. As a consequence, relative selectivity of the antidote determines its acceptable therapeutic windows. Independently of these two pharmacological parameters which are mainly under the influence of thermodynamic contribution, kinetics aspects are also important to take into consideration in order to promote a rapid neutralization of the anticoagulant, an additional criterion for the clinical practise. Last and not least, clearance rate of the antidote, and of its conjugate with heparin, is to be optimized in order to prevent long-term body accumulation while avoiding a too ephemeral pharmacological action.

Molecular Weight and Chemical Composition of the (Co-)Polymers

Molecular weight and chemical composition are important features which control the relative affinity and selectivity of polyelectrolyte complexes with heparin. In the first case, molecular weight controls the entire length of the (co-)polymers in a defined dissolution medium (ionic strength, pH, nature of salts, nature of counter-ions, . . . ) at a given temperature, in other words, its hydrodynamic diameter, but also its hydrodynamic shape and its relative flexibility (i.e. its ability to change from (local) conformation to promote future interaction with a polyanion chain). The total length of the polymer also affects the free energy balance resulting from the release of low-molecular weight counter-ions initially associated to the (co-)polymers in favor of the formation of a polyelectrolyte assembly with the polyanion chain.

Figure 7:
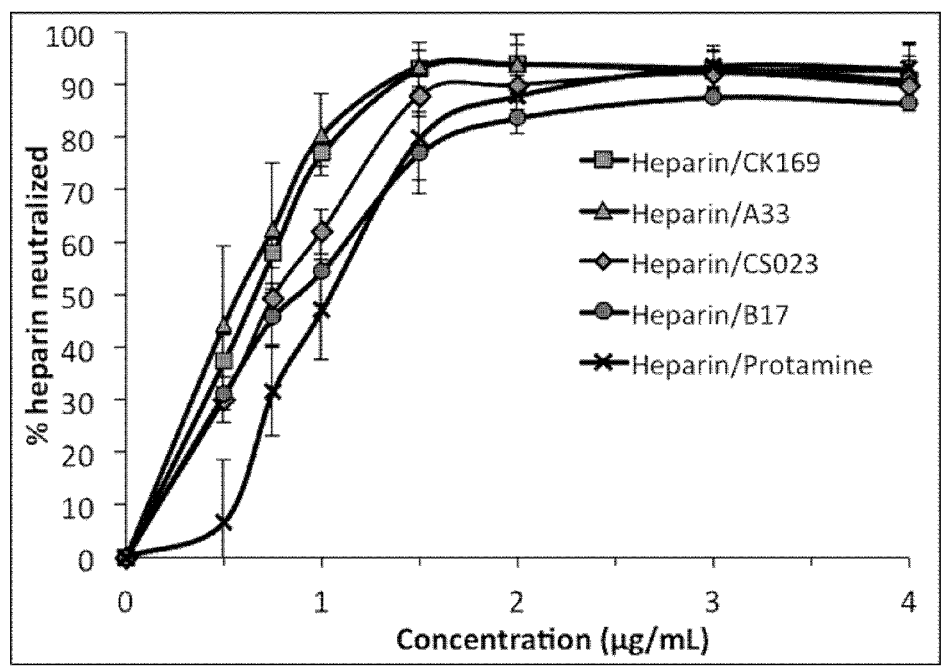
FIG. 7 shows dose-response curves of protamine, samples CS023, CK169, A33 and B17 versus neutralized fraction of UFH using aPTT bioassay.

The length of polymer was increased adopting either homopolymers of DMAEMA (CS023 and CK169), either block copolymer of PEO-PDMAEMA (B17 and A33), with a molecular range from 4,350 to 14,200 (Table 4). The copolymers were obtained by initiating the polymerization with an oligomer of PEO with a Mn of 510 Da. Hence their composition is made essentially from DMAEMA units, with a PEO chain at their alpha-extremity. Their respective dose-response curves highlight a similar profile corresponding to a rectangular hyperbola with a maximal value of UFH neutralization of more than 90% for a polymer concentration of 2 µg/mL (FIG. 7). The comparison of the IC50 (Table 4) clearly demonstrates a higher efficiency of the 4 synthetic (co-)polymers compared to the reference, protamine sulfate. Indeed in this range of UFH concentration at least, the IC50 of the PDMAEMA's of higher molecular weight (A33 and CK169) is about 2 times less than for protamine (0.55 µg/mL versus 1.05 µg/mL respectively). This difference in neutralization efficiency is also noted with the C$_{Max}$ values which are 1.60 µg/mL and 3.00 µg/mL for CK169 and protamine respectively. Interestingly but surprisingly enough none of these samples give rise to a quantitative neutralization of UFH. Indeed for all the dose/response curves the maximum % of UFH neutralization is around 90% irrespectively of the polymer nature. We also observed a slight potency decrease (10%) of the high molecular weight synthetic polymers (A33 and CK169) beyond 2 µg/mL, while a plateau is observed for protamine, CS023 and B17.

By comparison with UFH neutralization assay done in human plasma (FIG. 5, example 4), we observed that the presence of blood cells (in particular red blood cells and platelets which are highly concentrated in blood and well-known to be negatively charged), do not interfere significantly with the pharmacological activity of the synthetic (co-)polymers. Indeed whatever their presence or not, the optimal weight ratio between UFH and (co-)polymers to mostly inhibit the anticoagulation activity is around 1 to 1.3 (2 µg/mL of heparin for 1.5 to 2 µg/mL of (co-)polymer).

Mean Charge Density of the (Co-)Polymers

The charge density of (co-)polymers also plays a key role for their interaction with heparin, but also with other electronegative elements present in whole blood (cells, plasma proteins). Polymer charge density is here taken as the ratio between the amount of charged and the total monomers.

Figure 8:
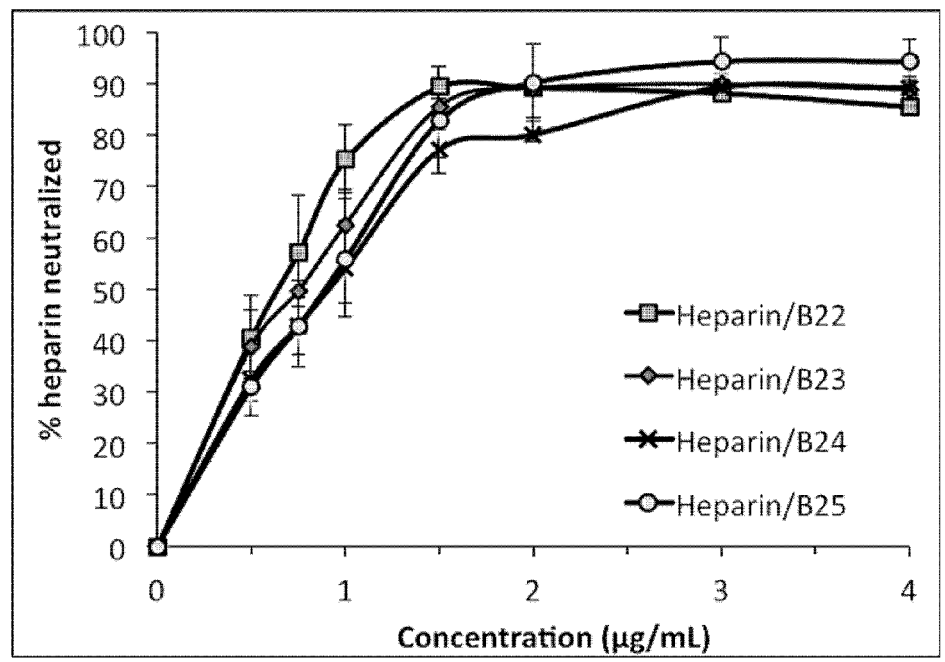
FIG. 8 shows dose-response curves of samples B22, B23, B24 and B25 versus neutralized fraction of UFH using aPTT bioassay.
Figure 9:
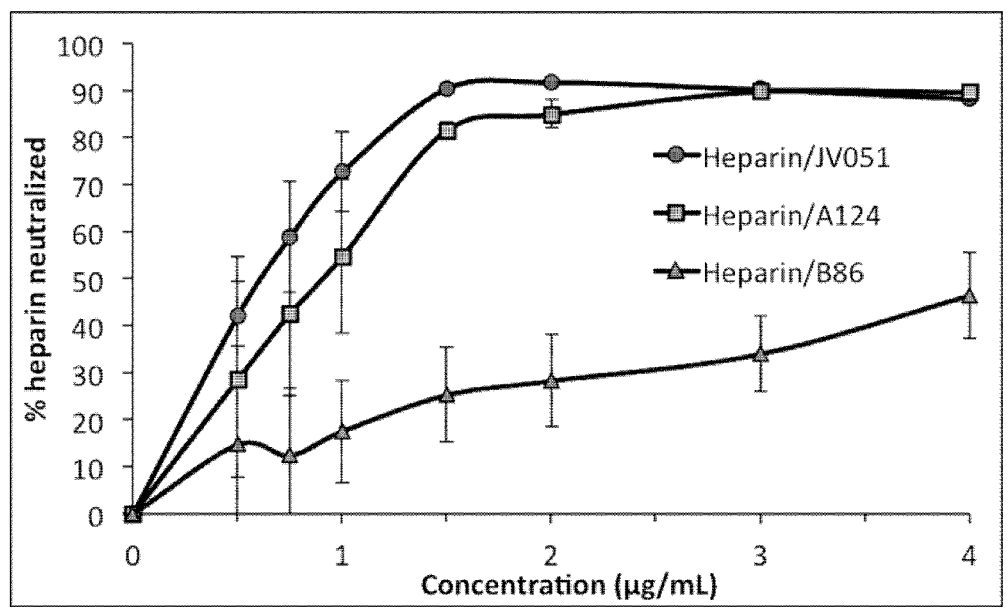
FIG. 9 shows dose-response curves of samples JV051, A124 and B86 versus neutralized fraction of UFH using aPTT bioassay.
Figure 10:
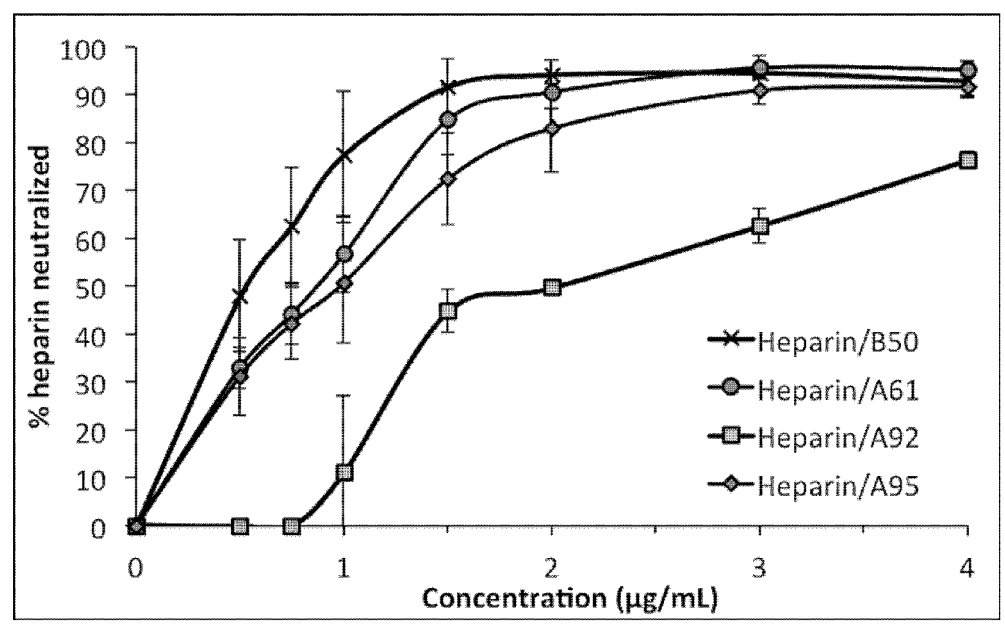
FIG. 10 shows dose-response curves of samples B50, A61, A92 and A95 versus neutralized fraction of UFH using aPTT bioassay.

With a mean pKa around 6.7, thus lower than physiological pH, it can be estimated that two thirds of the repetitive unit of PDMAEMA remain unprotonated in physiological environment. In view to increase the mean charge density of PDMAEMA on UFH neutralization keeping constant its molecular weight and composition, a progressive quaternization of the ternary amino-groups was done, generating the 3 polymers listed in Table 5 (B23, B24, and B25) starting from the homopolymer PDMAEMA B22 which has a Mn of 14,000 Da. Their neutralization efficiencies to UFH were tested in identical experimental conditions as previously with whole human blood. If all dose-response curves have the same similar profile of the rectangular hyperbole already noticed on FIG. 7, in opposite to our initial expectations these curves are significantly shifted towards higher IC50 when raising the mean charge density of the polymers from 30 to 80% (FIG. 8 and Table 5).

TABLE 5

| Code | Mn (g/mol) | Charge density (%) | Structure | Proportion DMAEMA (wt %) | IC$_{50}$ (µg/mL) | Max (µg/mL) |
|---|---|---|---|---|---|---|
| B22 | 14,000 | 30 | linear | 100 | 0.65 | 1.60 |
| B23 | 14,000 | 48 | linear | 100 | 0.75 | 1.60 |
| B24 | 14,000 | 65 | linear | 100 | 0.85 | 3.00 |
| B25 | 14,000 | 80 | linear | 100 | 0.85 | 3.00 |

We could indeed anticipate that raising the number of positive charges per chain of PDMAEMA would increase its affinity for UFH. In practice, the opposite situation is observed. Giving rise to a maximum for B22 and B23 as already noticed for the PDMAEMA samples CK169 and the PEO-b-PDMAEMA sample A33, the neutralization percentage of B24 and B25 increases asymptotically with a plateau phase. Although only slightly differences in neutralization effectiveness are noted, these differences are significant and reproducible between different blood donors.

Chemical Composition and Architecture of the (Co-)Polymers

Polyelectrolyte complex condensation capacity is not only related to the charge density of the interacting polymers but is also function of charge distribution, polymer backbone flexibility, and hydrophobicity/hydrophilicity balance. In view to alter the conformation of PDMAEMA, in particular to restrict its open structure and to graft some steric segments able to limit any nonspecific interactions with plasma proteins, alternative structures to linear PDMAEMA were evaluated in vitro. The macromolecular features of these PDMAEMA-based (co-)polymers are summarized in Table 6. 3 random PDMAEMA-co-MAPEO copolymers and 2 palm-tree PDMAEMA-co-MAPEO copolymers were investigated in order to evaluate the steric effect brought by the polyethylene oxide sequence on UHF neutralization. These copolymers were obtained by copolymerization of DMAEMA with methacrylate-terminated poly(ethylene oxide) (MAPEO).

characterized by MAPEO content as high as 74 wt %, the antidote efficiency and effectiveness are substantially reduced compared to the rest of the copolymers investigated. This drop in pharmacological efficiency of this polymer is explained by only 14 cationic sites per macromolecule. Based on the total repetitive units (MAPEO+DMAEMA) present within this macromolecule, this composition corresponds to a mean charge density of positive charges of only 3% of the repetitive units at neutral pH, therefore equivalent to a 10 fold decrease compared to a homopolymer of PDMAEMA.

For palm-tree architecture (FIG. 9), a similar evolution in the dose response curve is observed, with a progressive decrease in neutralization efficiency and effectiveness when raising the MAPEO content. Interestingly enough both polymers assessed lead to more than 90% of UFH neutralization. By comparison with the random copolymers none of the curves highlight an inhibition of the antidote action beyond the maximum titration.

In view to further reinforce the condensation of PDMAEMA in an aqueous medium, methyl methacrylate (MMA) units were incorporated in the PDMAEMA backbone with random distribution (A92 and A95 copolymers). For these two copolymers, PEO segments were also introduced by copolymerization with MAPEO.

TABLE 6

| Code | Mn copolymer (g/mol) | Mn (PEO) | Structure | Proportion DMAEMA (wt %) | Proportion MMA (wt %)) | $IC_{50}$ (µg/mL) | $C_{Max}$ (µg/mL) |
| --- | --- | --- | --- | --- | --- | --- | --- |
| JV051 | 18,500 | 1,100 | grafted | 88 | 0 | 0.65 | 2.00 |
| A124 | 19,300 | 1,385 | grafted | 72 | 0 | 0.85 | 1.70 |
| B86 | 29,100 | 455 | grafted | 26 | 0 | — | 4.00 |
| B50 | 19,800 | 455 | palm tree | 91 | 0 | 0.52 | 3.00 |
| A61 | 24,100 | 455 | palm tree | 78 | 0 | 0.80 | 3.00 |
| A92 | 12,500 | 510 | grafted + MMA | 72 | 16 | 2.00 | 4.00 |
| A95 | 18,400 | 1385 | grafted + MMA | 70 | 13 | 1.00 | 3.00 |

The brush-like polymer architecture of random copolymer provides better steric performance with a structure theoretically more favorable to stretch the polymer backbone. Expecting that a statistical distribution of the PEO grafts along the PDMAEMA backbone could better hamper the ionic interaction of the copolymer with plasma protein, three graft copolymers, i.e. JV051, A124 and B86 were assessed in vitro. Alternatively pseudo-block copolymer structure, A61 and B50, were also evaluated. Under the form of a palm tree organization, their PEO moieties are sufficiently separated from the cationic sequence.

The dose-response curves of UFH with the different content in PEO sequences of the random graft copolymers clearly indicates a progressive reduction in polyelectrolyte formation when raising the weight ratio of the PEO sequence in the copolymer (FIG. 8). With a content of MAPEO of only 12 wt % (JV051), the curve is almost superimposable to the homopolymer PDMAEMA CK169. With a content of 28 wt % of MAPEO (A124), neutralization of UFH gives rise to similar pharmacological profile as protamine sulfate, thus characterized by a higher IC50 (0.85 µg/mL) and with the absence of any maximum. If a neutralization of UFH is still occurring with B86, a copolymer The introduction of about 15 wt % of hydrophobic monomer unit of MMA within these copolymers does not impair their water solubility and does not either influence their interaction with UFH as shown by a similar dose response curve for A95 as for their palm-tree homologue PDMAEMA-g-MAPEO. The lower efficiency and effectiveness obtained with A92 can only be explained by its lower molecular weight (12,500 Da) which is about 1.5 to 2 times lower compared to the other copolymers assessed in this group.

Although a comparison in the macromolecular features is not strictly limited to one parameter, the lack of significant difference in efficiency between copolymer A61 and A124 illustrates that the range of molecular weight of PEO assess (i.e. 455 to 1,385) does not change significantly the functionality of these copolymers. This result illustrates that it is more the decrease in mean charge density than the repulsion action of PEO which contributes to modify the neutralization effectiveness.

Conclusion: The efficiency and effectiveness of the polymer of formula (I) for heparin neutralization in whole human blood is excellent. Dose-response curves carried out in whole human blood reveal the high affinity of different polymers of formula (I) for UFH allowing to successfully neutralize UFH with a higher efficiency compared to protamine. About half the concentration of polymer versus the concentration of protamine is needed to lead to 50% of maximal capacity to neutralize UFH.

By comparison with UFH neutralization assay done in human plasma, the presence of human blood cells do not interfere significantly with the pharmacological activity of the polymer of formula (I). The optimal weight ratio between UFH and polymer to mostly inhibit the anticoagulation activity is around 1 to 1.3.

Example 10

The neutralization performances of the (co-)polymers of formula (I) were further tested on blood collected from human patients who have been heparinized in vivo. The dose-response curves are presented in FIG. 11. Compared to the in vitro spiking of whole blood with heparin, the in vivo administration of UFH on human patients can significantly modify the availability of UFH through its biodistribution, interaction with various non-specific or specific receptors but also via its clearance from the blood compartment and whole body. Moreover, we can assume that the pharmacokinetics of UFH could change between patients and with pathologies, potentially leading to variability in pharmacological response of the anticoagulant antidote.

In example 10, several (co-)polymers of formula (I), namely two linear homopolymers of PDMAEMA (samples CS023 and CK169) and two copolymers of PDMAEMA and PEO (samples A61 and BA003) were tested for neutralization of UFH injected on human patients subjected to Extra-Corporeal Circulation (ECC) during a cardiovascular surgical operation. According to the general practice in this clinical context, a fixed dose of 3 mg/kg of UFH is administrated to these patients by intravenous injection. Neglecting any possible absorption, clearance of this anticoagulant dose theoretically corresponds to a maximal UFH concentration of 45 μg/mL in whole human blood within the first minutes post-injection.

10 min after this dose injection of UFH, 40 ml of whole blood were collected from the patients. In vitro UFH neutralization was conducted less than 1 hour after blood collection adding one of the (co-)polymers listed in Table 7. The concentration of these polymers ranged from 3.4 to 45 μg/mL in whole blood. A special care was taken during the addition of (co-)polymer solutions in view to ensure a rapid and reproducible homogenization of these (co-)polymers in whole human blood (rapid injection of the solution in whole human blood, i.e. in less than 1 s), followed directly by 3 up-and-down aspirations to avoid any risk of local over-concentrations.

After a 15 minutes incubation period performed at 37° C. under lateral agitation the aPTT test was carried out immediately in order to determine the residual UFH activity. The neutralization effectiveness of the different homopolymers and copolymers of protamine was estimated from the determination of $C_{Max}$, i.e. the minimal polymer concentration giving rise to a maximum neutralization of UFH. Therapeutic index ($Th_{ind}$) of the (co-)polymers was established as the drug concentration window giving a pharmacological effect without impairing the coagulation pathways. The results are listed in Table 7. The mean and standard deviations corresponding to these 3 parameters were calculated from 4 independent experiments performed on senior blood patients.

TABLE 7

| Code | Mn (co)polymer (g/mol) | Mn (PEO) | Structure | Proportion DMAEMA (wt %) | $C_{Max}$ (μg/mL) | aPTT at $C_{Max}$ (sec) | $Th_{Ind}$ (μg/mL) |
|---|---|---|---|---|---|---|---|
| CS023 | 4,350 | — | linear | 100 | 15 | 36.5 | 15 to 23 |
| CK169 | 10,100 | — | linear | 100 | 15 | 36.3 | 9 to 23 |
| A61 | 24,100 | 455 | palm tree | 78 | 15 | 28.5 | 15 to 34 |
| BA003 | 12,308 | 526 | statistics | 70 | 22.5 | 40.1 | 15 to 34 |
| B25 quaternized | 14,100 | — | linear | 100 | 22.5 | 38.9 | 15 to 45 |
| Protamine | 4,000 | — | linear | — | 22.5 | 42.7 | 15 to 45 |

The dose-response curves of FIG. 11 show that below a final concentration of 5 μg/mL none of the polymers affect the aPTT response. At this concentration, protamine does not—affect the aPTT response. At a concentration of 9 μg/mL a significant neutralization of UFH is illustrated for the homopolymer CK169 (aPTT below 100 s). A moderate neutralization is observed for the copolymer A61 (aPTT below 200 s). Surprisingly enough, neutralization of UFH is effective for all polymers at a $C_{Max}$ of 15 μg/mL, with an aPTT response slightly above the physiological values. This $C_{Max}$ value is up to 3 times less than the value estimated based on the theoretical maximum concentration of UFH in the blood (45 μm/mL) and the optimal weight ratio between UFH and polymers determined from example 9 to be around 1 to 1.3. As already observed in example 9, at concentration higher than $C_{Max}$ (34 μg/mL), a significant increase of aPTT response is observed for the two linear PDMAEMA's (CK169 and CS023), indicating an inhibition of the polymer action. Above this concentration, aPTT response is not anymore measurable, indicating a total inhibition of the coagulation.

By comparison, protamine also gives rise to a slight inhibition above its $C_{Max}$, thus above 22.5 μg/mL, while its level of interference on coagulation remains weak with an aPTT response which remains below 70 s for protamine concentration of 45 μg/mL.

We also assessed the pharmacological potency of the PDMAEMA quaternized coded B25, having a charge density of 80%, and of two PDMAEMA-PEO copolymers: BA003 and A61, containing 30 and 22% of PEO, distributed either in a random or palm tree structure respectively. The dose response curves of BA003 and A61 present a profile closer to that of protamine (FIG. 11). From these results, we illustrate that the introduction of PEO chains or the increase in positive charge density in the polymer is beneficial to prevent the coagulation inhibition. A total inhibition of aPTT response is nevertheless illustrated at the highest concentration assessed (45 μg/mL).

From the comparison of the 3 pharmacological parameters listed in Table 7, i.e. $C_{Max}$, aPTT at $C_{Max}$ and $Th_{ind}$, the most preferred (co-)polymers, are the PDMAEMA quaternized with a charge density of 80% (B25) and the copolymer PDMAEMA-PEO with palm-tree structure (A61). Those lead to the best compromise between affinity, potency and selectivity to neutralize UFH.

Example 11

In example 11, in vivo experiments were performed on Sprague Dawley rats in order to verify the safety of a polymer of formula (I), namely the linear homopolymer PDMAEMA (samples CK169 and CS023 detailed in previous examples). The samples were injected intravenously at a dose of 3 mg/kg, after injection of UFH at the same dose. This biocompatibility study was assessed on a short term basis, i.e. 24 hours after rat exposure to PDMAEMA, analyzing several blood biological parameters. Protamine sulfate was adopted as a reference to the polymer of formula (I).

This preclinical study was carried out on 20 Sprague Dawley rats (225 g) separated in three groups as detailed in Table 8. All rats received a first injection of 200 μL of UFH (50 μg/mL, final concentration in blood) in their tail vein. After 5 minutes, they received a second injection of an identical volume and concentration in the same vein. For the first group, this second injection consisted of protamine, while it consisted of PDMAEMA (samples CK169 and CS023 at 50 μg/mL final concentration in blood) for the second and third group respectively. A slow flow rate of 0.5 mL/min was adopted to inject the polymer solutions to limit any local over-concentrations. Blood was collected via saphena vena or from the ventricle of the heart respectively at time 0 (before all injections) or after 24 h. Afterwards the rat was euthanized.

Biological parameters evaluated on rat blood after injections are listed in Table 9. Data were acquired with the IStat clinical system. The normal ranges of concentrations given in this Table 9 for each parameter were taken from literature (minimal delay between blood collection and analysis <2 minutes). Two types of cartridge were used to evaluate the potential toxicity of PDMAEMA: CHEM 8 and CG4. The first one allowed to evaluate the metabolic status and renal function of the rats. The second cartridge allowed to measure the blood acid/base status and to detect any tissue hypoxia or hyperlactatemia. A counter-analysis of rat blood cells was also done to measure hemocompatibility.

TABLE 8

| Rats groups | UFH | Group 1 Protamine | Group 2 CS023 | Group 3 CK169 |
|---|---|---|---|---|
| 1-5 (protamine group) | injection | injection | | |
| 6-10 (CS023 group) | injection | | injection | |
| 11-15 (CK169 group) | injection | | | injection |

TABLE 9

| Parameters | Control | | PDMAEMA | | |
| | T0 | Normal ranges | CS023 | CK169 | Protamine |
|---|---|---|---|---|---|
| pH and oxygenation | | | | | |
| pH | 7.4 | 7.25-7.38 | 7.4 | 7.4 | 7.4 |
| pO$_2$ (mmHg) | 45.0 (+/−5.0) | 26-54 | 25.0 (+/−1.0) | 30.0 (+/−5.0) | 30.0 (+/−3.0) |
| pCO$_2$ (mmHg) | 37.0 (+/−3.0) | 12-58 | 45.5 (+/−3.7) | 42.7 (+/−2.8) | 42.7 (+/−3.7) |
| HCO$_3$ (mmol/L) | 22.0 (+/−4.0) | 12.2-25.4 | 28.0 (+/−2.0) | 28.0 (+/−2.0) | 30.0 (+/−3.0) |
| Chemistry/electrolytes | | | | | |
| Sodium (mmol/L) | 150 (+/−3.0) | 142-163 | 150 (+−/2.0) | 150 (+−/0.0) | 150 (+/−2.0) |
| Chloride (mmol/L) | 108.3 (+/−0.1) | 100-110 | 105.0 (+/−0.1) | 108.3 (+/−0.1) | 108.3 (+/−0.1) |
| Potassium (mmol/L) | 4.4 (+/−0.4) | 2.6-4.3 | 4.4 (+/−0.2) | 4.0 (+/−0.2) | 4.4 (+/−0.2) |
| Ionized calcium (mmol/L) | 0.8 (+/−0.2) | 0.27-1.26 | 1.4 (+/−0.3) | 1.3 (+/−0.2) | 1.4 (+/−0.1) |
| Glucose (mmol/L) | 7.0 (+/−1.0) | 4.4-16 | 15.0 (+/−1.0) | 12.0 (+/−3.0) | 13.0 (+/−0.1) |
| Urea nitrogen (mg/dL) | 16.0 (+/−1.1) | 15-21 | 17.0 (+/−0.5) | 17.5 (+/−2.3) | 21.5 (+/−1.0) |
| Creatinine (mg/dL) | 0.25 (+/−0.02) | 0.2-0.8 | 0.35 (+/−0.05) | 0.42 (+/−0.02) | 0.40 (+/−0.02) |
| Hematology | | | | | |
| WBC (×10$^3$ μL) | 8.3 (+/−1.0) | 3-17 | 5.0 (+/−0.2) | 4.7 (+/−0.3) | 2.5 (+/−0.1) |
| RBC (×10$^6$ μL) | 6.4 (+/−0.4) | 5-10 | 5.0 (+/−0.1) | 5.6 (+/−0.2) | 6.0 (+/−0.4) |
| Platelets (×10$^3$ μL) | 650.0 (+/−100.0) | 995-1713 | 1000.0 (+/−20.0) | 800 (+/−50.0) | 650.0 (+/−100.0) |
| Hematocrit (%) | 37.5 (+/−2.5) | 35-57 | 32.5 (+/−0.1) | 35.0 (+/−0.1) | 35.0 (+/−2.5) |

In order to trace any toxicological side effects after injection of the polymer of formula (I), the in viva investigation comprised many different parameters of rat blood.

The first category of bioassays, i.e. pH, blood gases ($pO_2$, $pCO_2$) and $HCO_3^-$, reflect potential acid-base disturbance in the body as indicator of a cardio-pulmonary or kidney dysfunction. The comparison of the data between initial values and after exposure of the rats to PDMAEMA demonstrates that blood pH remains perfectly constant and is equal to 7.4 for all rats tested. There is a significant drop in blood $pO_2$ (25 mmHg for CS023 and 30 mmHg for CK169) which is correlated with an increase in $pCO_2$ and $HCO_3^-$ compared to the initial values (45 mmHg for $pO_2$). However those changes were observed for all PDMAEMA and protamine treated rats and remain within acceptable values extracted from the literature (26-54 mmHg for $pO_2$, 12-58 mmHg for $pCO_2$ and 12.2-25.4 mmHg for $HCO_3^-$). It is also worth to mention that these parameters can be significantly affected by other physiological parameters, such as stress possibly occurring during the in vivo test. To conclude for these first parameters, the injection of PDMAEMA does not impair the acid-base balance of the blood in the time scale of investigation.

Sodium, chloride and potassium electrolytes were measured, as their variation in concentration could indicate renal or cardiac failure. The obtained values remain stable with no significant difference between the three groups of rats. Such alteration in the physiology of the rats can thus be rejected.

Ionized calcium was also measured. It may have an implication in critical physico-biochemical mechanisms, such as blood coagulation, nerve conduction, neuromuscular transmission and muscle contraction. An increase in ionized calcium is illustrated for the three rats groups compared to time 0 with values respectively equal to 1.3 and 0.8 mmol/L. The value after treatment is slightly above the normal range found in the literature (0.27-1.26 mmol/L). We did not observe any direct consequence on the rats potentially linked to this alteration.

Glucose is a primary energy source for the body and the only source of nutrients for brain tissue. One cause for increase in glucose is the stress. An increase in glucose content was observed for all treated rats compared to time 0. The value is still within the normal range found in the literature (4.4-16 mmol/L).

Urea nitrogen and creatinine were assessed in view to investigate potential damage in renal function. Elevated levels of creatinine or urea nitrogen in the blood are mainly associated with abnormal kidney function. As for glucose content, a significant increase is observed in all rats treated, in particular for creatinine which raised from 0.25 to approximately 0.40 mg/dL but these values remain in the acceptable values for rats (15-21 mg/dL for urea nitrogen and 0.2-0.8 mg/dL for creatinine).

Regarding hematology parameters, the rat red blood cells (RBC) population remains relatively constant (both in terms of hemoglobin content and in RBC's counting), while a decrease in the rat white blood cells (WBC) population is noticed in all three rats groups, in particular after protamine sulfate administration ($2.5\times10^3$ μL compared to the initial value of $8.3\times10^3$ μL). A significant increase in platelets ($1000\times10^3$ μL for sample CS023 compared to the initial value of $650\times10^3$ μL) was further observed but all these values remain within the acceptable range taken from literature (3-17×$10^3$ μL for WBC and 995-1713×$10^3$ μL for platelets).

Example 12

In example 12, a pharmacological study was carried out in vivo on Sprague Dawley rats in experimental conditions similar to example 11 but for the purpose to verify the neutralization efficiency of UFH by two polymers of formula (I), namely PDMAEMA (samples CS23 and CK169 already described in previous examples).

The Polymers have been injected intravenously at a dose of 3 mg/Kg following an i.v. inoculation of UFH administrated at the same dose, 5 minutes before the polymer injection.

Kinetics of UFH neutralisation has been assessed collecting blood samples at 35 min, 125 min and 24 h after rat exposure to the polymers. Protamine sulfate (same dose as the polymers) and saline (PBS) were adopted as positive and negative controls respectively.

In practice, this preclinical study was carried out on 30 Sprague Dawley rats (225 g) separated in 5 groups detailed on TABLE 10. This inoculation was realized by injection first 200 μL of UFH (50 μg/mL, final concentration in blood) in the tail vein of the animal. 5 min later an identical volume and concentration of protamine or PDMAMEA (50 μg/mL, final concentration in blood) was perfused in the same vein of the rats. A slow flow rate of 0.5 ml/min was adopted to inject the polymer to limit any local over-concentration.

Blood was collected via saphena vena at time 35 min, 125 min, and 24 h before proceeding to the rat euthanasia. Coagulation parameters of the rats were measured by:

The activated partial thromboplastin time (APTT): indicator measuring the efficacy of both the "intrinsic" and the common coagulation pathways. It is widely used to monitor the treatment with heparin (UFH).

Anti Xa assay used for monitoring patients on UFH but also LMWH. Although UFH is commonly monitored by APTT, in some cases this test can undervalue the degree of anticoagulation induced by the UFH and the measurement of a plasma anti-Xa level can provide a more precise assessment of anticoagulation.

Thereby, APTT and anti-Xa activity were measured on isolated plasma to evaluate the concentration of free heparin at 35 min, 125 min and 24 h.

TABLE 10

| Rats groups | Time sequence for injection | | | | |
|---|---|---|---|---|---|
| | Saline | UFH | Protamine | CKS023 | CK169 |
| 1-6 Saline group | injection | — | — | — | — |
| 7-12 UFH group | — | injection | — | — | — |
| 13-18 Protamine group | — | injection | injection | — | — |
| 19-24 CS023 group | — | injection | — | injection | — |
| 25-30 CK169 group | — | injection | — | — | injection |

Figure 12:
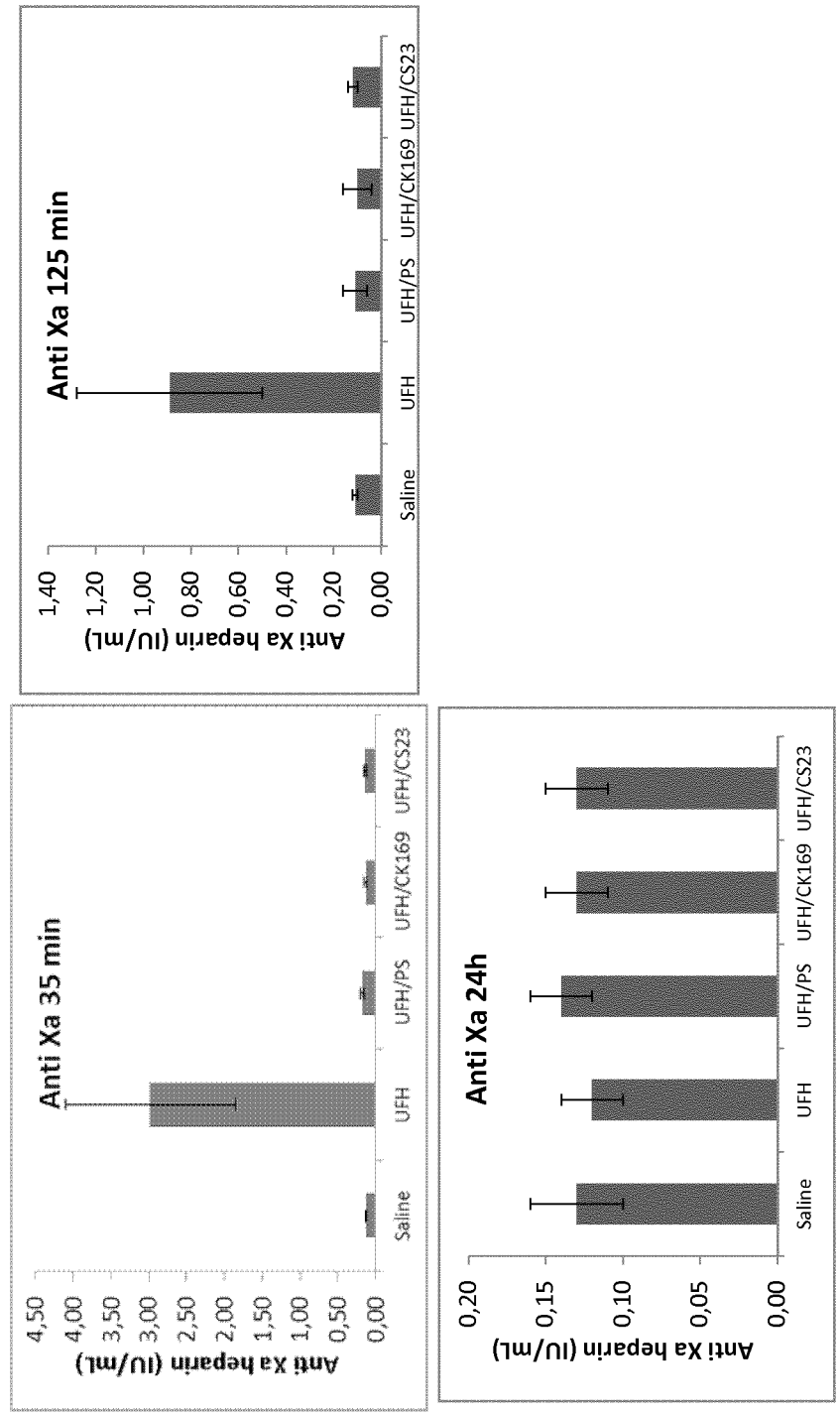
FIG. 12 shows anti Xa activity measured on rats at 35 min, 125 min and 24 h after i.v. injection of polymers. Protamine sulfate=PS; UFH=Unfractionated Heparin.
Figure 13:
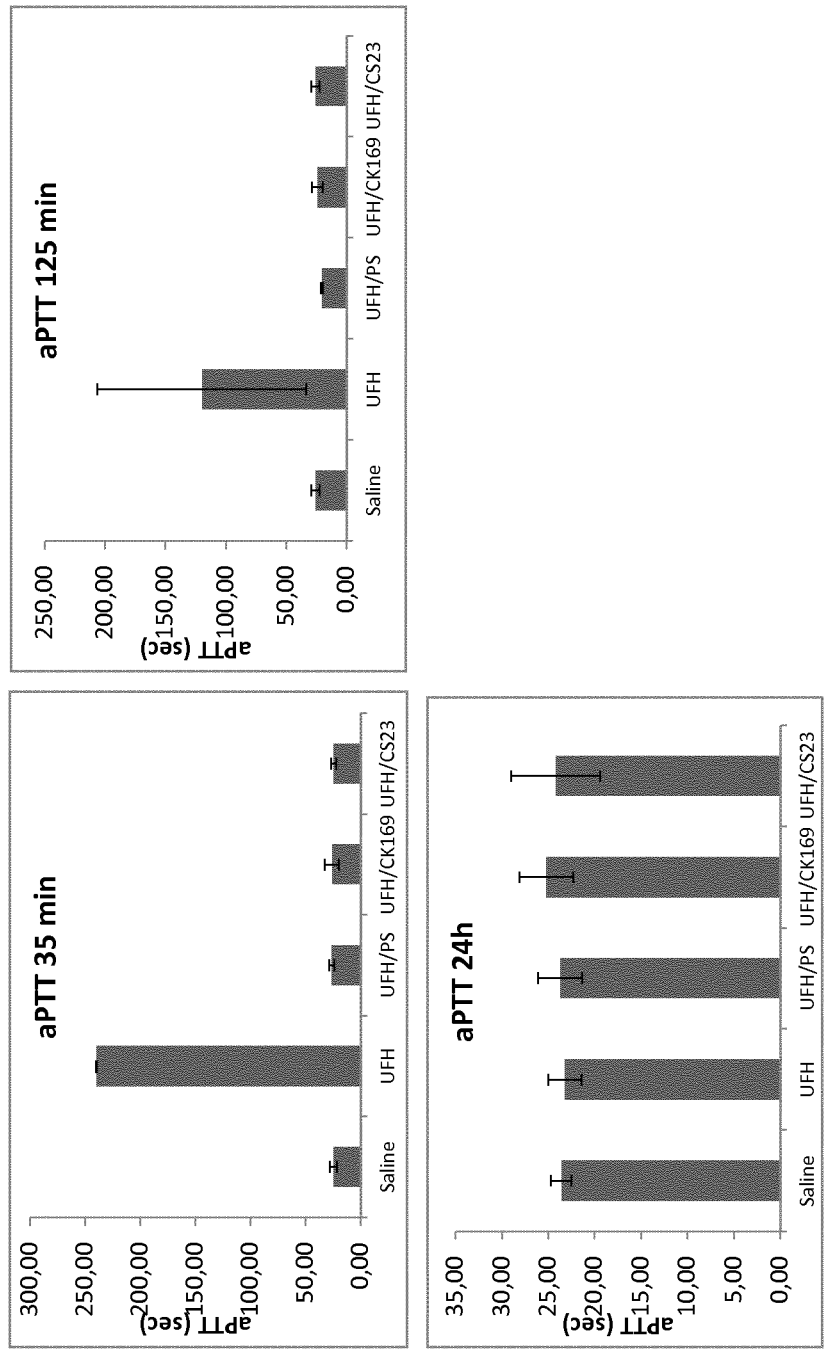
FIG. 13 shows Activated Partial thromboplastin timeactivity (APTT) at 35 min, 125 min and 24 h after i.v. injection of polymers. Protamine sulfate=PS; UFH=Unfractionated Heparin.

As a whole, considering the biological parameters investigated in this study, it can be stated from data represented on FIGS. 12 and 13 that the polymer of formula (I) assessed, PDMAEMA with two different molecular weights, has a similar pharmacological profile compared to protamine sulfate used as a reference.

The invention claimed is:

1. A polymer of formula (I):

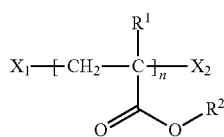

I where $X_1$ and $X_2$ respectively represent the alpha and omega end groups of the polymer;
$R^1$ represents a hydrogen atom or a straight or branched chain alkyl group from 1 to 6 carbon atoms;
$R^2$ represents a straight or branched chain alkyl group which is substituted by a group which has a positive charge at a physiological pH; and
n is an integer having a value from 6 to 130;
or a copolymer thereof;
for use as a medicament;
wherein $X_1$ and $X_2$ represent a hydrogen atom, a hydroxyl group, an ethyl isobutyrate group, an alkyl group, an halogen group, a carboxylic acid group, an amino group or a methoxy or an ethoxy group.

2. The polymer according to claim 1, Wherein $R^2$ represents a straight or branched chain alkyl group comprising from 1 to 10 carbon atoms.

3. The polymer according to claim 1, wherein the substituent of $R^2$ has a positive charge at pH 7.4; and the substituent of $R^2$ is a group of formula —N($R^3$)$_2$ wherein $R^3$ is the same or different and represents a hydrogen atom or a straight or branched chain alkyl group from 1 to 6 carbon atoms.

4. The polymer according to claim 1, wherein the polymer is a co-polymer.

5. The polymer according to claim 4, wherein the co-polymer has a linear, dendritic, or grafted structure.

6. The polymer according to claim 4, wherein the co-polymer comprises a repetitive unit Which is one or more of an ethylene glycol, an acrylate, a methacrylate, optionally carrying a polyethylene oxide (PEO), or a unit —(CH$_2$—C($R^1$)(C(O)O$R^4$))— where $R^4$ represents a straight or branched chain alkyl group substituted by a group —N$^+$($R^3$)$_3$.

7. The polymer according to claim 1, which is a polymer of formula (IV):

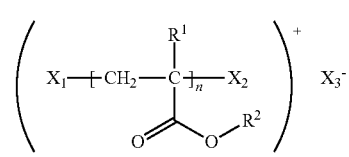

IV where $X_1$, $X_2$, $R^1$, $R^2$ and n are as defined in claim 1; and $X_3$ represents an anion, for example $OH^-$; $Cl^-$; $HCO_3^-$; $NO_3^-$; $H_2PO_4^-$.

8. The polymer according to claim 1, Which is in lyophilisate form.

9. The polymer according to claim 1, which has a mean charge density of from 20 to 80%.

10. The polymer according to claim 9, which has a mean charge density from 15 to 30%.

11. The polymer according to claim 1, which has a molecular weight from 4000 to 10000 g/mol.

12. The polymer according to claim 1 which comprises a repetitive unit which is N,N dimethyl amino ethyl methacrylate.

13. The polymer according to claim 12 which is polydimethyl amino ethyl methacrylate.

14. A method for treatment of a heparin overdose and/or for neutralisation of anticoagulation comprising the step of administering the polymer according to claim 1 to a subject.

15. A pharmaceutical composition comprising a polymer of formula (I) as claimed in claim 1 and a pharmaceutically acceptable diluent for use as a medicament.

16. A method of treating a heparin overdose or for neutralising anticoagulation which method comprises a step of administering to a human or animal in need of such treatment an effective amount of a polymer of formula (I) as defined in claim 1.

17. A method of treating a heparin overdose or for neutralising anticoagulation which method comprises a step of administering to a human or animal in need of such treatment an effective amount of a pharmaceutical composition as defined in claim 15.

18. The polymer according to claim 1, wherein $X_1$ is an ethylisobutyrate moiety, $X_2$ is a hydroxyl group, $R^1$ is a methyl group or a variant thereof, $R^2$ is a straight alkyl group comprising two carbon atoms substituted by a group of formula $-N(R^3)_2$ wherein $R^3$ represents a hydrogen atom or a straight or branched chain alkyl group having from 1 to 6 carbon atoms, n is an integer having a value from 6 to 130, $X_3$ is a chloride anion or a variant thereof.

\* \* \* \* \*